US011529292B2

(12) United States Patent
Pratt et al.

(10) Patent No.: US 11,529,292 B2
(45) Date of Patent: *Dec. 20, 2022

(54) COMPOSITIONS IN THE FORM OF DISSOLVABLE SOLID STRUCTURES

(71) Applicant: The Procter & Gamble Company, Cincinnati, OH (US)

(72) Inventors: Michael Sean Pratt, Cincinnati, OH (US); Jennifer Elaine Hilvert, Cincinnati, OH (US); Pamela Ann Keune, West Chester, OH (US); Alessandra Massa, Cincinnati, OH (US); Melanie Anne Kay, Hamilton, OH (US); Mark William Hamersky, Hamilton, OH (US); Mark Robert Sivik, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/838,692

(22) Filed: Jun. 13, 2022

(65) Prior Publication Data

US 2022/0323309 A1    Oct. 13, 2022

Related U.S. Application Data

(63) Continuation of application No. 16/431,115, filed on Jun. 4, 2019, now Pat. No. 11,395,789, which is a continuation of application No. PCT/US2018/015364, filed on Jan. 26, 2018.

(60) Provisional application No. 62/451,237, filed on Jan. 27, 2017.

(51) Int. Cl.
| | |
|---|---|
| *A61K 8/02* | (2006.01) |
| *A61K 8/46* | (2006.01) |
| *A61K 8/81* | (2006.01) |
| *A61Q 5/00* | (2006.01) |
| *A61Q 11/00* | (2006.01) |
| *A61Q 19/00* | (2006.01) |
| *A61Q 5/02* | (2006.01) |
| *A61Q 5/12* | (2006.01) |
| *A61K 8/49* | (2006.01) |

(52) U.S. Cl.
CPC ............ *A61K 8/027* (2013.01); *A61K 8/0216* (2013.01); *A61K 8/463* (2013.01); *A61K 8/4993* (2013.01); *A61K 8/8129* (2013.01); *A61Q 5/00* (2013.01); *A61Q 5/02* (2013.01); *A61Q 5/12* (2013.01); *A61Q 11/00* (2013.01); *A61Q 19/00* (2013.01); *A61K 2800/222* (2013.01); *A61K 2800/412* (2013.01); *A61K 2800/596* (2013.01)

(58) Field of Classification Search
CPC combination set(s) only.
See application file for complete search history.

(56) References Cited

U.S. PATENT DOCUMENTS

| | | | |
|---|---|---|---|
| 1,421,350 | A | 6/1922 | Powell |
| 2,356,168 | A | 8/1944 | Mabley |
| 2,396,278 | A | 3/1946 | Otto |
| 2,438,091 | A | 3/1948 | Lynch |
| 2,486,921 | A | 11/1949 | Byerly |
| 2,486,922 | A | 11/1949 | Bruce |
| 2,528,378 | A | 10/1950 | Mannheimer |
| 2,613,185 | A | 10/1952 | Marshall |
| 2,658,072 | A | 11/1953 | Milton |
| 2,694,668 | A | 11/1954 | Fricke |
| 2,809,971 | A | 10/1957 | Jack et al. |
| 3,152,046 | A | 10/1964 | Maria |
| 3,236,733 | A | 2/1966 | Karsten et al. |
| 3,321,425 | A | 5/1967 | Karl-ludwig et al. |
| 3,332,880 | A | 7/1967 | Adriaan et al. |
| 3,426,440 | A | 2/1969 | Shen et al. |
| 3,428,478 | A | 2/1969 | Donaldson et al. |
| 3,463,308 | A | 8/1969 | Deneke |
| 3,489,688 | A | 1/1970 | Pospischil |
| 3,570,122 | A | 3/1971 | Willimas |
| 3,589,007 | A | 6/1971 | Walton |
| 3,653,383 | A | 4/1972 | Wise |
| 3,695,989 | A | 10/1972 | Albert |
| 3,753,196 | A | 8/1973 | Kurtz et al. |
| 3,761,418 | A | 9/1973 | Parran |
| 3,929,678 | A | 12/1975 | Laughlin |
| 3,967,921 | A | 7/1976 | Haberli et al. |
| 4,020,156 | A | 4/1977 | Murray et al. |
| 4,024,078 | A | 5/1977 | Gilbert et al. |

(Continued)

FOREIGN PATENT DOCUMENTS

| | | |
|---|---|---|
| CA | 169627 S | 5/2018 |
| CN | 1138091 | 12/1996 |

(Continued)

OTHER PUBLICATIONS

"Green Chemistry", Huazhong University of Science and Technology Press, published on Jun. 30, 2008, pp. 6.
Adhesives Research (Pennsylvania, http://12.4.33.51/news/apresmed.htm).
All final and non-final office actions for U.S. Appl. No. 29/728,688 (P&G Case D-02862).
All Office Actions; U.S. Appl. No. 14/690,593, filed Apr. 20, 2015.
All Office Actions; U.S. Appl. No. 15/665,886, filed Aug. 1, 2017.
All Office Actions; U.S. Appl. No. 15/979,961, filed May 15, 2018.

(Continued)

*Primary Examiner* — Hasan S Ahmed
(74) *Attorney, Agent, or Firm* — Alexandra S. Anoff

(57) ABSTRACT

Described are effervescent dissolvable solid structures having fibers formed from a composition comprising surfactant and water soluble polymeric structurant, having a total dissolvable solid structure density of from about 0.100 g/cm³ to about 0.380 g/cm³, having a surfactant dose of from about 0.5 to about 2.0 g, and a surfactant density of from about 0.1 g/cm³ to about 0.3 g/cm³. Also described are processes for manufacturing the Dissolvable Solid Structure.

20 Claims, 11 Drawing Sheets

(56) References Cited

U.S. PATENT DOCUMENTS

| | | |
|---|---|---|
| 4,051,081 A | 9/1977 | Jabs et al. |
| 4,089,945 A | 5/1978 | Brinkman et al. |
| 4,149,551 A | 4/1979 | Benjamin et al. |
| 4,185,125 A | 1/1980 | Kimura et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,323,683 A | 4/1982 | Bolich, Jr. et al. |
| 4,345,080 A | 8/1982 | Bolich, Jr. |
| D266,829 S | 11/1982 | Yoshizawa et al. |
| 4,379,753 A | 4/1983 | Bolich, Jr. |
| 4,381,919 A | 5/1983 | Jacquet et al. |
| 4,422,853 A | 12/1983 | Jacquet et al. |
| 4,470,982 A | 9/1984 | Winkler |
| 4,507,280 A | 3/1985 | Pohl et al. |
| 4,529,586 A | 7/1985 | De et al. |
| 4,536,361 A | 8/1985 | Torobin |
| 4,565,647 A | 1/1986 | Llenado |
| D286,450 S | 10/1986 | Tovey |
| 4,635,351 A | 1/1987 | Koch et al. |
| 4,663,158 A | 5/1987 | Wolfram et al. |
| 4,710,374 A | 12/1987 | Grollier et al. |
| 4,723,362 A | 2/1988 | Boerger |
| 4,727,410 A | 2/1988 | Higgins, III |
| 4,822,613 A | 4/1989 | Rodero |
| 4,885,107 A | 12/1989 | Wetzel |
| 4,976,953 A | 12/1990 | Orr et al. |
| 4,990,280 A | 2/1991 | Thorengaard |
| 5,055,384 A | 10/1991 | Kuehnert |
| 5,061,481 A | 10/1991 | Suzuki et al. |
| 5,062,889 A | 11/1991 | Hoehl et al. |
| 5,062,994 A | 11/1991 | Imperatori |
| 5,094,853 A | 3/1992 | Hagarty |
| 5,098,636 A | 3/1992 | Balk |
| 5,100,657 A | 3/1992 | Ansher-jackson et al. |
| 5,100,658 A | 3/1992 | Bolich, Jr. et al. |
| 5,102,129 A | 4/1992 | Roberts |
| 5,104,646 A | 4/1992 | Bolich, Jr. |
| 5,106,609 A | 4/1992 | Bolich, Jr. |
| 5,166,276 A | 11/1992 | Hayama et al. |
| D334,420 S | 3/1993 | Copeland et al. |
| 5,220,033 A | 6/1993 | Kamei et al. |
| 5,261,426 A | 11/1993 | Kellett et al. |
| 5,280,079 A | 1/1994 | Allen et al. |
| RE34,584 E | 4/1994 | Grote et al. |
| D351,345 S | 10/1994 | Geho |
| 5,391,368 A | 2/1995 | Gerstein |
| D357,115 S | 4/1995 | Ashley et al. |
| 5,409,703 A | 4/1995 | Mcanalley et al. |
| D358,025 S | 5/1995 | Martin et al. |
| 5,415,810 A | 5/1995 | Lee |
| 5,429,628 A | 7/1995 | Trinh et al. |
| 5,455,114 A | 10/1995 | Ohmory |
| 5,457,895 A | 10/1995 | Thompson et al. |
| 5,458,433 A | 10/1995 | Stastny |
| 5,476,597 A | 12/1995 | Sakata et al. |
| 5,501,238 A | 3/1996 | Von Borstel et al. |
| 5,533,636 A | 7/1996 | Reiker |
| 5,580,481 A | 12/1996 | Sakata et al. |
| 5,582,786 A | 12/1996 | Brunskill et al. |
| D378,180 S | 2/1997 | Hayes |
| 5,660,845 A | 8/1997 | Trinh et al. |
| 5,672,576 A | 9/1997 | Behrens et al. |
| 5,673,576 A | 10/1997 | Chen et al. |
| 5,674,478 A | 10/1997 | Dodd |
| 5,750,122 A | 5/1998 | Evans |
| 5,780,047 A | 7/1998 | Kamiya et al. |
| D398,847 S | 9/1998 | Wyslotsky |
| D399,260 S | 10/1998 | Thimote |
| 5,849,378 A | 12/1998 | Gask |
| D407,640 S | 4/1999 | Crapser et al. |
| D408,223 S | 4/1999 | Henry |
| 5,911,224 A | 6/1999 | Berger |
| 5,925,603 A | 7/1999 | D'Angelo |
| 5,955,419 A | 9/1999 | Barket, Jr. et al. |
| D416,103 S | 11/1999 | Hashmi |
| 5,976,454 A | 11/1999 | Sterzel et al. |
| D418,415 S | 1/2000 | Hayes |
| D418,750 S | 1/2000 | Blin |
| 6,010,719 A | 1/2000 | Remon et al. |
| 6,029,808 A | 2/2000 | Peck et al. |
| 6,034,043 A | 3/2000 | Fujiwara |
| D427,902 S | 7/2000 | Hayes |
| 6,106,849 A | 8/2000 | Malkan et al. |
| 6,177,391 B1 | 1/2001 | Zafar |
| 6,200,949 B1 | 3/2001 | Reijmer et al. |
| D441,869 S | 5/2001 | Bloor et al. |
| D442,353 S | 5/2001 | Macias |
| D442,739 S | 5/2001 | Friesenhahn |
| D443,389 S | 6/2001 | Friesenhahn |
| D448,802 S | 10/2001 | Lariviere, Jr. et al. |
| D449,881 S | 10/2001 | Mock, Sr. |
| D450,378 S | 11/2001 | Minakuchi et al. |
| 6,365,142 B1 | 4/2002 | Tamura |
| D462,900 S | 9/2002 | Yamada et al. |
| 6,458,754 B1 | 10/2002 | Velazquez et al. |
| D465,303 S | 11/2002 | Friesenhahn |
| 6,503,521 B1 | 1/2003 | Atis et al. |
| 6,525,034 B2 | 2/2003 | Dalrymple et al. |
| D479,561 S | 9/2003 | Meyer |
| D484,749 S | 1/2004 | Garraway |
| D489,162 S | 5/2004 | Dings-plooij |
| 6,790,814 B1 | 9/2004 | Marin |
| 6,800,295 B2 | 10/2004 | Fox |
| 6,802,295 B2 | 10/2004 | Bedwell et al. |
| 6,808,375 B2 | 10/2004 | Kloetzer |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| D509,935 S | 9/2005 | Burt |
| 6,943,200 B1 | 9/2005 | Corrand et al. |
| D515,915 S | 2/2006 | Karim |
| 7,015,181 B2 | 3/2006 | Lambino |
| 7,208,460 B2 | 4/2007 | Shefer et al. |
| D549,051 S | 8/2007 | Nordwall |
| 7,285,520 B2 | 10/2007 | Krzysik |
| 7,387,787 B2 | 6/2008 | Fox |
| D576,753 S | 9/2008 | Mukai |
| D577,332 S | 9/2008 | Moore |
| D578,881 S | 10/2008 | Friedland |
| D588,332 S | 3/2009 | Phelan |
| 7,832,552 B2 | 11/2010 | Newman |
| 7,846,462 B2 | 12/2010 | Spadini et al. |
| 7,892,992 B2 | 2/2011 | Kamada et al. |
| 7,901,696 B2 | 3/2011 | Eknoian et al. |
| D640,921 S | 7/2011 | Caldwell |
| D644,541 S | 9/2011 | Schrader et al. |
| D651,096 S | 12/2011 | Nakagiri |
| D655,154 S | 3/2012 | Amos |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butler et al. |
| 8,367,596 B2 | 2/2013 | Fossum et al. |
| D680,882 S | 4/2013 | Logue |
| 8,415,287 B2 | 4/2013 | Glenn, Jr. et al. |
| D682,622 S | 5/2013 | Keys |
| 8,461,090 B2 | 6/2013 | Glenn, Jr. et al. |
| 8,461,091 B2 | 6/2013 | Glenn, Jr. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,541,081 B1 | 9/2013 | Ranganathan et al. |
| 8,546,640 B2 | 10/2013 | Popovsky et al. |
| D694,621 S | 12/2013 | Mccarthy |
| 8,723,333 B2 | 5/2014 | Park et al. |

(56) References Cited

U.S. PATENT DOCUMENTS

| | | |
|---|---|---|
| 8,765,170 B2 | 7/2014 | Glenn, Jr. |
| D712,159 S | 9/2014 | Clerici et al. |
| D712,822 S | 9/2014 | Brusaw et al. |
| 9,062,186 B2 | 6/2015 | Longdon et al. |
| D739,227 S | 9/2015 | Mitchell et al. |
| D740,928 S | 10/2015 | Bruining et al. |
| 9,198,838 B2 | 12/2015 | Glenn, Jr. |
| D748,240 S | 1/2016 | Goode |
| D769,522 S | 10/2016 | Venet |
| D771,788 S | 11/2016 | Duckwitz |
| D774,086 S | 12/2016 | Montes et al. |
| D775,198 S | 12/2016 | Montes et al. |
| 9,539,444 B2 | 1/2017 | Kinoshita et al. |
| D778,026 S | 2/2017 | Roetheli |
| D793,025 S | 8/2017 | Slusarczyk et al. |
| D797,551 S | 9/2017 | Chatterton |
| D798,143 S | 9/2017 | Chatterton |
| D808,583 S | 1/2018 | Zietek |
| D811,922 S | 3/2018 | Lefave |
| D811,935 S | 3/2018 | Hughes |
| D819,836 S | 6/2018 | Noël |
| D848,102 S | 5/2019 | Carlson et al. |
| D850,041 S | 5/2019 | Endle |
| 10,294,586 B2 | 5/2019 | Sivik et al. |
| D851,344 S | 6/2019 | Carlson et al. |
| D857,156 S | 8/2019 | Hani |
| D857,242 S | 8/2019 | Darrow et al. |
| D857,929 S | 8/2019 | Darrow et al. |
| D862,020 S | 10/2019 | Gorrell et al. |
| D863,600 S | 10/2019 | Chao |
| D864,507 S | 10/2019 | Stoughton et al. |
| D866,105 S | 11/2019 | Carlson et al. |
| D866,891 S | 11/2019 | Carlson et al. |
| D866,892 S | 11/2019 | Hunt et al. |
| D866,893 S | 11/2019 | Hunt et al. |
| D867,717 S | 11/2019 | Chavez |
| D868,159 S | 11/2019 | Swisher et al. |
| D868,953 S | 12/2019 | Mckendree |
| 10,569,286 B2 | 2/2020 | Anderson et al. |
| D878,694 S | 3/2020 | Carlson et al. |
| 10,694,917 B2 | 6/2020 | Dreher et al. |
| D901,115 S | 11/2020 | Carlson et al. |
| D903,152 S | 11/2020 | Chao |
| D906,802 S | 1/2021 | Chi |
| D910,434 S | 2/2021 | Tan et al. |
| D910,457 S | 2/2021 | Lee |
| D921,166 S | 6/2021 | Meyers |
| D933,095 S | 10/2021 | Heiner et al. |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada et al. |
| 2002/0187181 A1 | 12/2002 | Godbey et al. |
| 2003/0018242 A1 | 1/2003 | Hursh et al. |
| 2003/0032573 A1 | 2/2003 | Tanner et al. |
| 2003/0045441 A1 | 3/2003 | Hsu et al. |
| 2003/0069154 A1 | 4/2003 | Hsu et al. |
| 2003/0080150 A1 | 5/2003 | Cowan |
| 2003/0099691 A1 | 5/2003 | Lydzinski et al. |
| 2003/0099692 A1 | 5/2003 | Lydzinski et al. |
| 2003/0141662 A1 | 7/2003 | Kost et al. |
| 2003/0166489 A1 | 9/2003 | Van et al. |
| 2003/0180242 A1 | 9/2003 | Eccard et al. |
| 2003/0186826 A1 | 10/2003 | Eccard et al. |
| 2003/0194416 A1 | 10/2003 | Shefer |
| 2003/0199412 A1 | 10/2003 | Gupta |
| 2003/0207776 A1 | 11/2003 | Shefer et al. |
| 2003/0209166 A1 | 11/2003 | Vanmaele et al. |
| 2003/0215522 A1 | 11/2003 | Johnson et al. |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0048771 A1 | 3/2004 | Mcdermott |
| 2004/0053808 A1 | 3/2004 | Raehse et al. |
| 2004/0059055 A1 | 3/2004 | Inada |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey et al. |
| 2004/0118852 A1 | 6/2004 | Barmore et al. |
| 2004/0126585 A1 | 7/2004 | Kerins et al. |
| 2004/0175404 A1 | 9/2004 | Shefer |
| 2004/0180597 A1 | 9/2004 | Kamada |
| 2004/0202632 A1 | 10/2004 | Gott et al. |
| 2004/0206270 A1 | 10/2004 | Vanmaele et al. |
| 2004/0242097 A1 | 12/2004 | Hasenoehrl |
| 2004/0242772 A1 | 12/2004 | Huth et al. |
| 2005/0069575 A1 | 3/2005 | Fox |
| 2005/0118237 A1 | 6/2005 | Krzysik et al. |
| 2005/0136780 A1 | 6/2005 | Clark et al. |
| 2005/0137272 A1 | 6/2005 | Gaserod |
| 2005/0159730 A1 | 7/2005 | Kathrani et al. |
| 2005/0202992 A1 | 9/2005 | Grandio et al. |
| 2005/0220745 A1 | 10/2005 | Lu |
| 2005/0232954 A1 | 10/2005 | Yoshinari et al. |
| 2005/0272836 A1 | 12/2005 | Yaginuma et al. |
| 2005/0287106 A1 | 12/2005 | Legendre |
| 2006/0002880 A1 | 1/2006 | Peffly et al. |
| 2006/0013869 A1 | 1/2006 | Ignatious |
| 2006/0052263 A1 | 3/2006 | Roreger et al. |
| 2006/0064510 A1 | 3/2006 | Low et al. |
| 2006/0078528 A1 | 4/2006 | Yang et al. |
| 2006/0078529 A1 | 4/2006 | Uchida et al. |
| 2006/0128592 A1 | 6/2006 | Ross |
| 2006/0159730 A1 | 7/2006 | Simon |
| 2006/0228319 A1 | 10/2006 | Vona, Jr. et al. |
| 2006/0274263 A1 | 12/2006 | Yacktman et al. |
| 2007/0028939 A1 | 2/2007 | Mareri et al. |
| 2007/0099813 A1 | 5/2007 | Luizzi |
| 2007/0110792 A9 | 5/2007 | Simon |
| 2007/0135528 A1 | 6/2007 | Butler et al. |
| 2007/0149435 A1 | 6/2007 | Koenig et al. |
| 2007/0225388 A1 | 9/2007 | Cooper et al. |
| 2008/0019935 A1 | 1/2008 | Khan |
| 2008/0035174 A1 | 2/2008 | Aubrun-sonneville |
| 2008/0083420 A1 | 4/2008 | Glenn et al. |
| 2008/0090939 A1 | 4/2008 | Netravali et al. |
| 2008/0131695 A1 | 6/2008 | Aouad et al. |
| 2008/0138492 A1 | 6/2008 | Cingotti |
| 2008/0152894 A1 | 6/2008 | Beihoffer et al. |
| 2008/0153730 A1 | 6/2008 | Tsaur |
| 2008/0215023 A1 | 9/2008 | Scavone et al. |
| 2008/0276178 A1 | 11/2008 | Fadell et al. |
| 2008/0292669 A1 | 11/2008 | Deng et al. |
| 2008/0293839 A1 | 11/2008 | Stobby |
| 2009/0197787 A1 | 8/2009 | Venet et al. |
| 2009/0232873 A1 | 9/2009 | Glenn, Jr. et al. |
| 2009/0263342 A1 | 10/2009 | Glenn, Jr. |
| 2010/0018641 A1 | 1/2010 | Branham |
| 2010/0150976 A1 | 6/2010 | Schnitzler |
| 2010/0167971 A1 | 7/2010 | Glenn, Jr. et al. |
| 2010/0173817 A1 | 7/2010 | Glenn, Jr. et al. |
| 2010/0179083 A1 | 7/2010 | Glenn, Jr. et al. |
| 2010/0279905 A1 | 11/2010 | Glenn, Jr. |
| 2010/0286011 A1 | 11/2010 | Glenn, Jr. et al. |
| 2010/0291165 A1 | 11/2010 | Glenn, Jr. et al. |
| 2011/0023240 A1 | 2/2011 | Fossum |
| 2011/0027328 A1 | 2/2011 | Baig et al. |
| 2011/0028373 A1 | 2/2011 | Fossum et al. |
| 2011/0028374 A1 | 2/2011 | Fossum et al. |
| 2011/0033509 A1 | 2/2011 | Simon |
| 2011/0165110 A1 | 7/2011 | Kinoshita et al. |
| 2011/0182956 A1 | 7/2011 | Glenn, Jr. et al. |
| 2011/0189246 A1 | 8/2011 | Glenn, Jr. et al. |
| 2011/0189247 A1 | 8/2011 | Glenn, Jr. |
| 2011/0195098 A1 | 8/2011 | Glenn, Jr. |
| 2011/0250256 A1 | 10/2011 | Hyun-oh et al. |
| 2011/0287687 A1 | 11/2011 | Kramer et al. |
| 2012/0021026 A1 | 1/2012 | Glenn, Jr. |
| 2012/0052036 A1 | 3/2012 | Glenn, Jr. |
| 2012/0052037 A1 | 3/2012 | Sivik et al. |
| 2012/0107534 A1 | 5/2012 | Wnuk et al. |

(56) References Cited

U.S. PATENT DOCUMENTS

| | | |
|---|---|---|
| 2012/0237576 A1 | 9/2012 | Gordon |
| 2012/0270029 A1 | 10/2012 | Glenn, Jr. et al. |
| 2012/0288693 A1 | 11/2012 | Stanley et al. |
| 2012/0294823 A1 | 11/2012 | Aramwit |
| 2012/0321580 A1 | 12/2012 | Glenn, Jr. |
| 2013/0236520 A1 | 9/2013 | Popovsky et al. |
| 2013/0303419 A1 | 11/2013 | Glenn, Jr. et al. |
| 2014/0105946 A1 | 4/2014 | Glenn, Jr. et al. |
| 2014/0271744 A1 | 9/2014 | Glenn, Jr. et al. |
| 2014/0329428 A1 | 11/2014 | Glenn, Jr. |
| 2015/0102307 A1 | 4/2015 | Tajima et al. |
| 2015/0297494 A1 | 10/2015 | Mao |
| 2015/0313803 A1 | 11/2015 | Lynch et al. |
| 2015/0313804 A1 | 11/2015 | Lynch et al. |
| 2015/0313805 A1 | 11/2015 | Lynch et al. |
| 2015/0313806 A1 | 11/2015 | Lynch et al. |
| 2015/0313807 A1 | 11/2015 | Lynch et al. |
| 2015/0313808 A1 | 11/2015 | Lynch et al. |
| 2015/0313809 A1 | 11/2015 | Lynch et al. |
| 2015/0315350 A1 | 11/2015 | Mao et al. |
| 2016/0008235 A1 | 1/2016 | Sivik et al. |
| 2016/0101026 A1 | 4/2016 | Pratt |
| 2016/0101204 A1 | 4/2016 | Lynch |
| 2016/0143827 A1 | 5/2016 | Castan Barberan et al. |
| 2016/0250109 A1 | 9/2016 | Dreher et al. |
| 2016/0367104 A1 | 12/2016 | Dreher et al. |
| 2017/0121641 A1 | 5/2017 | Smith |
| 2017/0335080 A1 | 11/2017 | Mao et al. |
| 2018/0110710 A1 | 4/2018 | Zhao et al. |
| 2018/0140469 A1 | 5/2018 | Kane et al. |
| 2018/0311135 A1 | 11/2018 | Chang et al. |
| 2018/0333339 A1 | 11/2018 | Hamersky |
| 2018/0334644 A1 | 11/2018 | Hamersky et al. |
| 2019/0015875 A1 | 1/2019 | Gardner, Jr. et al. |
| 2019/0282457 A1 | 9/2019 | Pratt |
| 2019/0282461 A1 | 9/2019 | Glassmeyer |
| 2019/0350819 A1 | 11/2019 | Hamersky et al. |
| 2020/0093710 A1 | 3/2020 | Hamersky |
| 2020/0214946 A1 | 7/2020 | Chan et al. |
| 2020/0308360 A1 | 10/2020 | Mao et al. |
| 2020/0405587 A1 | 12/2020 | Song |
| 2021/0000733 A1 | 1/2021 | Hilvert |
| 2021/0094744 A1 | 4/2021 | Benson et al. |
| 2021/0107263 A1 | 4/2021 | Bartolucci et al. |
| 2021/0147763 A1 | 5/2021 | Tan et al. |
| 2021/0401677 A1 | 12/2021 | Song |

FOREIGN PATENT DOCUMENTS

| | | |
|---|---|---|
| CN | 1219388 | 6/1999 |
| CN | 1268558 | 10/2000 |
| CN | 1357613 A | 7/2002 |
| CN | 1454231 A | 11/2003 |
| CN | 1473194 A | 2/2004 |
| CN | 1530431 A | 9/2004 |
| CN | 1583991 A | 2/2005 |
| CN | 1726074 A | 1/2006 |
| CN | 3648760 | 5/2007 |
| CN | 102006852 A | 4/2011 |
| CN | 301666535 | 9/2011 |
| CN | 102647973 A | 8/2012 |
| CN | 103282015 A | 9/2013 |
| CN | 103735428 A | 4/2014 |
| CN | 104040061 A | 9/2014 |
| CN | 304115833 | 4/2017 |
| CN | 106726634 A | 5/2017 |
| CN | 106728634 A | 5/2017 |
| CN | 304537587 | 3/2018 |
| CN | 109589279 B | 3/2020 |
| DE | 19607851 A1 | 9/1997 |
| DE | 10331767 A1 | 2/2005 |
| EP | 0392608 A2 | 10/1990 |
| EP | 609808 A1 | 8/1994 |
| EP | 0858828 A1 | 8/1998 |
| EP | 0948960 A2 | 10/1999 |
| EP | 1214879 A2 | 6/2002 |
| EP | 1217987 B1 | 12/2004 |
| EP | 1574561 A1 | 9/2005 |
| EP | 1160311 B1 | 3/2006 |
| EP | 1958532 A2 | 8/2008 |
| EP | 2085434 A1 | 8/2009 |
| EP | 1317916 B1 | 10/2010 |
| FR | 2871685 A1 | 12/2005 |
| FR | 2886845 A1 | 12/2006 |
| GB | 2235204 A | 2/1991 |
| GB | 2355008 A | 4/2001 |
| GB | 2378407 A | 2/2003 |
| JP | 58021608 | 2/1983 |
| JP | S58216109 | 12/1983 |
| JP | S6272609 A | 4/1987 |
| JP | S6272610 A | 4/1987 |
| JP | S6281432 A | 4/1987 |
| JP | H01172319 A | 7/1989 |
| JP | H01313418 A | 12/1989 |
| JP | H0275650 | 3/1990 |
| JP | H05344873 | 12/1993 |
| JP | H0617083 A | 1/1994 |
| JP | 0753349 | 2/1995 |
| JP | H0789852 A | 4/1995 |
| JP | H08325133 A | 12/1996 |
| JP | H09216909 A | 8/1997 |
| JP | H10251371 A | 9/1998 |
| JP | H11513053 A | 11/1999 |
| JP | 2000053998 A | 2/2000 |
| JP | 2000229841 A | 8/2000 |
| JP | 2001519376 A | 10/2001 |
| JP | 2001520983 A | 11/2001 |
| JP | 2002226895 A | 8/2002 |
| JP | 2003073700 A | 3/2003 |
| JP | 2003082397 A | 3/2003 |
| JP | 2004509198 A | 3/2004 |
| JP | 2004256799 A | 9/2004 |
| JP | 2004345983 A | 12/2004 |
| JP | 2005171063 A | 6/2005 |
| JP | 2005538202 A | 12/2005 |
| JP | 2006056835 A | 3/2006 |
| JP | 2007001889 A | 1/2007 |
| JP | 2007091954 A | 4/2007 |
| JP | 2007197365 A | 8/2007 |
| JP | 2007197540 A | 8/2007 |
| KR | 20020003442 A | 1/2002 |
| WO | 8301943 A1 | 6/1983 |
| WO | 9514495 A1 | 6/1995 |
| WO | 9951715 A1 | 10/1999 |
| WO | 0042992 A2 | 7/2000 |
| WO | 0107194 A1 | 2/2001 |
| WO | 0119948 A1 | 3/2001 |
| WO | 0125393 A1 | 4/2001 |
| WO | 200125322 A1 | 4/2001 |
| WO | 2001024770 A1 | 4/2001 |
| WO | 2001054667 A1 | 8/2001 |
| WO | 0238722 A2 | 5/2002 |
| WO | 2004032859 A1 | 4/2004 |
| WO | 2004041991 A1 | 5/2004 |
| WO | 2005003423 A1 | 1/2005 |
| WO | 2005070374 A1 | 8/2005 |
| WO | 2005075547 A1 | 8/2005 |
| WO | 2007033598 A1 | 3/2007 |
| WO | 2007093558 A1 | 8/2007 |
| WO | 2007102119 A1 | 9/2007 |
| WO | 2008104954 A2 | 9/2008 |
| WO | 2009019571 A2 | 2/2009 |
| WO | 2009095891 A1 | 8/2009 |
| WO | 2010077627 A2 | 7/2010 |
| WO | 2010085569 A1 | 7/2010 |
| WO | 2012120199 A1 | 9/2012 |
| WO | DM100932 | 4/2018 |
| WO | DM100938 | 4/2018 |
| WO | DM101063 | 5/2018 |
| WO | DM101100 | 5/2018 |

(56) References Cited

FOREIGN PATENT DOCUMENTS

| WO | DM101101 | 5/2018 |
|---|---|---|
| WO | 2019001940 A1 | 1/2019 |

OTHER PUBLICATIONS

All Office Actions; U.S. Appl. No. 15/981,096, filed May 16, 2018.
All Office Actions; U.S. Appl. No. 16/431,028, filed Jun. 4, 2019.
All Office Actions; U.S. Appl. No. 16/431,115, filed Jun. 4, 2019.
All Office Actions; U.S. Appl. No. 16/577,120, filed Sep. 20, 2019.
All Office Actions; U.S. Appl. No. 16/589,504, filed Oct. 1, 2019.
All Office Actions; U.S. Appl. No. 16/901,548, filed Jun. 15, 2020.
All Office Actions; U.S. Appl. No. 16/912,876, filed Jun. 26, 2020.
All Office Actions; U.S. Appl. No. 16/918,292, filed Jul. 1, 2020.
All Office Actions; U.S. Appl. No. 16/953,975, filed Nov. 20, 2020.
All Office Actions; U.S. Appl. No. 17/070,205, filed Oct. 14, 2020.
All Office Actions; U.S. Appl. No. 17/357,119, filed Jun. 24, 2021.
All Office Actions; U.S. Appl. No. 29/672,822, filed Dec. 10, 2018.
All Office Actions; U.S. Appl. No. 29/676,338, filed Jan. 10, 2019.
All Office Actions; U.S. Appl. No. 29/707,807, filed Oct. 1, 2019.
All Office Actions; U.S. Appl. No. 29/707,809, filed Oct. 1, 2019.
All Office Actions; U.S. Appl. No. 29/728,687, filed Mar. 20, 2020.
All Office Actions; U.S. Appl. No. 29/766,885, filed Jan. 19, 2021.
All Office Actions; U.S. Appl. No. 29/815,500, filed Nov. 15, 2021.
All Office Actions; U.S. Appl. No. 29/819,499, filed Dec. 15, 2021.
Amerilab Technologies, Inc. (Minnesota, http://www.amerilabtech.comm/).
Anonymous "P8136 Poly(vinyl alcohol)" Internet article, [Online] XP002538935, Retrieved from the Internet URL:hllp:/20 NWW.sigmaaldrich.com/catalog/ProductDetail.do?D7=0%N25-SEARCH_CONCAT PNOIBRAND KEY%N4=P8136%7SCIAL%N25=0% QS=ON%F=SPEC retrieved on Jul. 28, 2009, year 2009, 1 pg.
Briscoe et al. "The effects of hydrogen bonding upon the viscosity of aqueous poly( vinyl alcohol) solutions," from Polymer, 41 (2000), pp. 3851-3860.
Cardinal Health (Dublin, Ohio, http://spd.cardinal.com/).
Cima Labs, Inc. (Minnesota, http://www.cimalabs.com/).
Color Keeper [online], [site visited Oct. 18, 2021], Available from internet, URL: https://shopgemz.com/products/color-keeper?variant=13094595002434&utm_source=google&utm_medium=cpc&utm_campaign=Shopping&gclid=Cj0KCQjw5JSLBhCxARIsAHgO2SdAT7LTehpyxM1qTGtnFETDa1Nuo9_cQSOpPwCmsmmdGA1Y0USekQEaAh0iEALw_wcB (Year: 2021).
Definition of Derivative by Merriam Webster Online Dictionary, Year, 2021.
Design of "Detergent tablets" (Design Registration No. 000634142-0003), (No. of Publicly known information: HH18274488), Registered Community Designs Bulletin, published by EUIPO on Jan. 9, 2007, 4 pgs.
Design of "Detergent tablets" (Design Registration No. 000634142-0004), (No. of Publicly known information: HH18274489), Registered Community Designs Bulletin, published by EUIPO on Jan. 9, 2007, 4 pgs.
Design of "Soaps" accepted on Jul. 11, 1986, Publishing Office: Korean Intellectual Property Office (KIPO), Document Name: Design Gazette (Application No. 3019850005996), Publication Date: Jun. 9, 1986, (No. of Publicly known information: HG21900612), 3 pgs.
Dissolving Soap Strips (Ranir LLC, Michigan, www.ranir.com).
Dow, UCARE™ Polymer LR-400, Technical Data Sheet, Downloaded in Mar. 2022, 4 pages.
Encyclopedia of Polymer Science and Engineering, vol. 15, 2nd ed., pp. 204 308 Silicones, year 1989.
Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.
Hexagon 4 ward soap mold, Soap, Cosmetics, NEW Silicon mold, Published on Sep. 29, 2016, Retrieved from Internet :http://candlebox.com/product/%EC%9C%A1%EA%B0%81-4%EA%B5%AC-%EB%B9%84%EB%88%84%EB%AA%B0 %EB%93%9C/2206/?page_4=3#none, dated Sep. 10, 2019, 16 pgs.
Hildebrand, T., et al. "Quantification of bone microarchitecture with the structure mode index", Computer Methods in Biomechanics and Biomedical Engineering, vol. 1, Jan. 14, 1997, pp. 15-23.
How Gemz work?, Gemz Hair Care, published on Oct. 1, 2018, retrieved on Apr. 27, 2021, retrieved from the Internet URL: https://www.youtube.com/watch?v=ts1waYk43g4, 3 pgs.
Japanese Paper Soap (http://www.wishingfish.com/papersoap.html).
Karen Duis et al., "Environmental fate and effects of water-soluble synthetic organic polymers used in cosmetic products", Environmental Sciences Europe, vol. 33, Article No. 21, Feb. 16, 2021, 78 pages.
Kuraray: "Mowiol—Technical data sheet", Jun. 1, 2010 (Jun. 1, 2010),pp. 1-4, XP055119891, Retrieved from the Internet: URL:http://www.kuraray.eu/fileadmin/Downloads/mowiol/TDS_Mowiol_en_20110624.pdf [retrieved on May 23, 2014].
Le Laboratoire du Bain (France, http://www.laboudubain.com/).
M.K. Industries (Gujarat India, http://www.soapstrips.com).
Mana Okasaka, Evaluation of anionic surfactants effects on the skin barrier function based on skin permeability, Pharmaceutical Development and Technology, 24:1,99-104, published online: Jan. 23, 2018 (Year: 2018).
Megulars Car Wash Strips: Megulars Inc. California, http://www.automotivedigesl.com/view_art.asp?articles!D=12414.
Michelle Villett, Why You Need a Sulfate-Free Shampoo, The Skincare Edit, updated date: Jan. 25, 2019, original publication date: Feb. 22, 2016 (Year: 2016).
MOVA Pharmaceutical and Kosmos (USA, http:/lwww.icon-pr.com/news/news/prinl.cfm?inv_id=256-1).
Ni Genshan et al. "Drug Classification and Pharmacology Summary", PLA Press, published on Apr. 30, 1988, pp. 3.
Paper Pieces Hexagons, announced 2018 [online], [site visited Oct. 14, 2021]. Available from internet, URL:https://www.amazon.com/Paper-Pieces-HEX100B-Hexagons-1200pc/dp/B07DVYV2HN/ (Year: 2018).
Product Review: Gemz Solid Shampoo, Travel As Much, published on Mar. 19, 2019, retrieved on Apr. 27, 2021, retrieved from the Internet URL: https://travelasmuch.com/gemz-solid-shampoo-review/, 14 pgs.
Pure Soap Leafz: (Soap UNLTD. Netherlands, http://www.upandunder.com.uk/eshop/catalogue/testbs.asp? Manufacturer_ID=252&Activity_ID=33&Description_ID=157).
Raymond C Rowe et al., Polyvinyl Alcohol, Handbook of Pharmaceutical Excipients, 2009, Sixth Edition, Pharmaceutical Press, 564-565.
Retrieved from: https ://www.craftcuts.com/hexagon-craft-shape.html Hexagon wood cutouts, www.craftcuts.com, 1 page, reviewed as early as May 2018 (Year: 2018), 16 pgs.
Rounded hexagon shape, announced 2016 [online], [site visited Oct. 20, 2021], Available from internet, URL:https://www.vexels.com/png-svg/preview/139199/rounded-hexagon-shape (Year: 2016).
Sahin et al. "A Study on Physical and Chemical Properties of Cellulose Paper Immersed in Various Solvent Mixtures" International Journal Of Molecular Sciences, Jan. 2008; 9(1): 78-88.
Sanipro Sanitary Products (Italy, http://www.sanipro.iit).
Solublon (Toyohashi Japan, http://www.solublon.com).
SPI Pharma (Delaware, http://www.spipharma.com).
Travelers Passport Paper Soap Sheets (http://www.weddingflavornow.com/index.asp?PageAction=VIEWPROD&PROD&ProdID=510).
Vaughan, C.D. "Solubility, Effects in Product, Package, Penetration and Preservation", Cosmetics and Toiletries, vol. 103, Oct. 1988, 24 pgs.
Vesterby, A.: "Star Volume in Bone Research: A Histomorphometric Analysis Of Trabecular Bone Structure Using Vertical Sections", Anal Rec: Feb. 1993, 232(2), pp. 325-334.
Wenda (China, http://www.wenda.com).
Wermuth et al. Drug Discovery, "Drug Discovery Today, 2006", vol. 11 7/8, 348-354, Year 2006.
Zhang et al. "Study on Morphology of Electrospun Poly( vinyl alcohol) Mats," European Polymer Journal 41 (2005), pp. 423-432.
Hiroshi Yagi & 4 Others, Research Study of a Friction Protector for Preventing a Tow Line From Breaking,Working Papers for Fiscal 2006 | JAPAN | Japan Coast Guard Dec. 2007, pp. 1-8.

(56) References Cited

OTHER PUBLICATIONS

Latorre Carmen, Nanotribological Effects of Hair Careproducts and Environment on Human Hair Using Atomic ForceMicroscopy,Journal of Vacuum Science and Technology: Part A, U.S.A, AVS/AIP, Jun. 28, 2005, V2 3 N 4, p. 1034-1045.

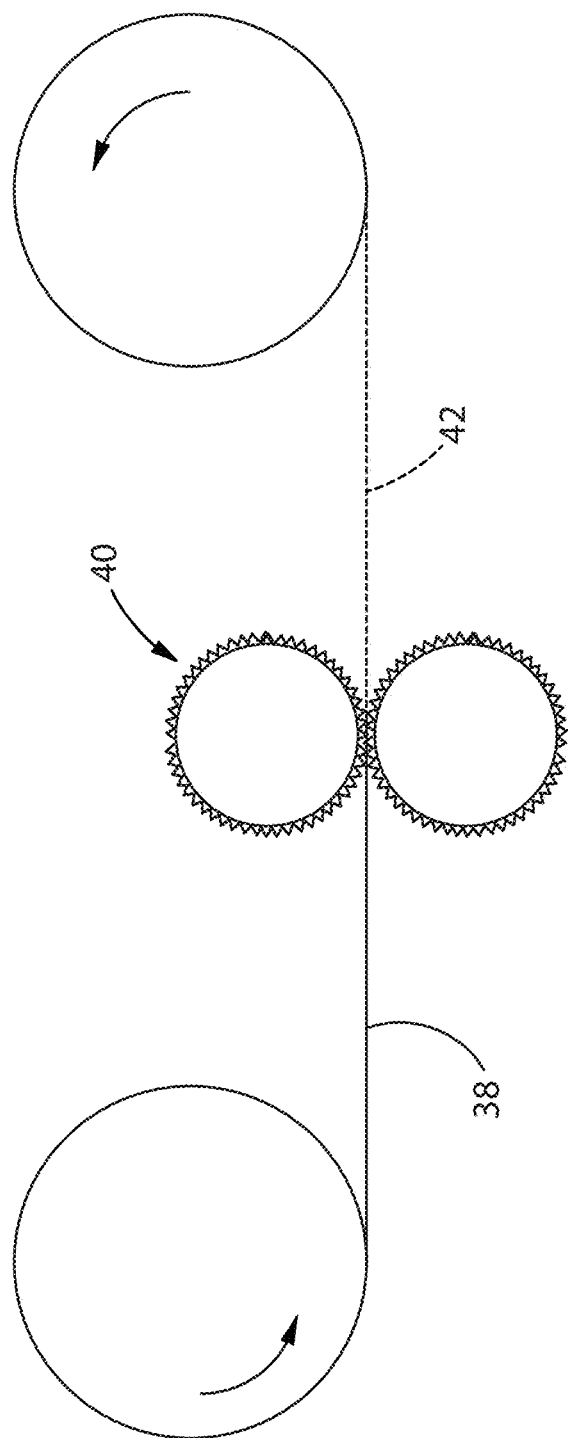

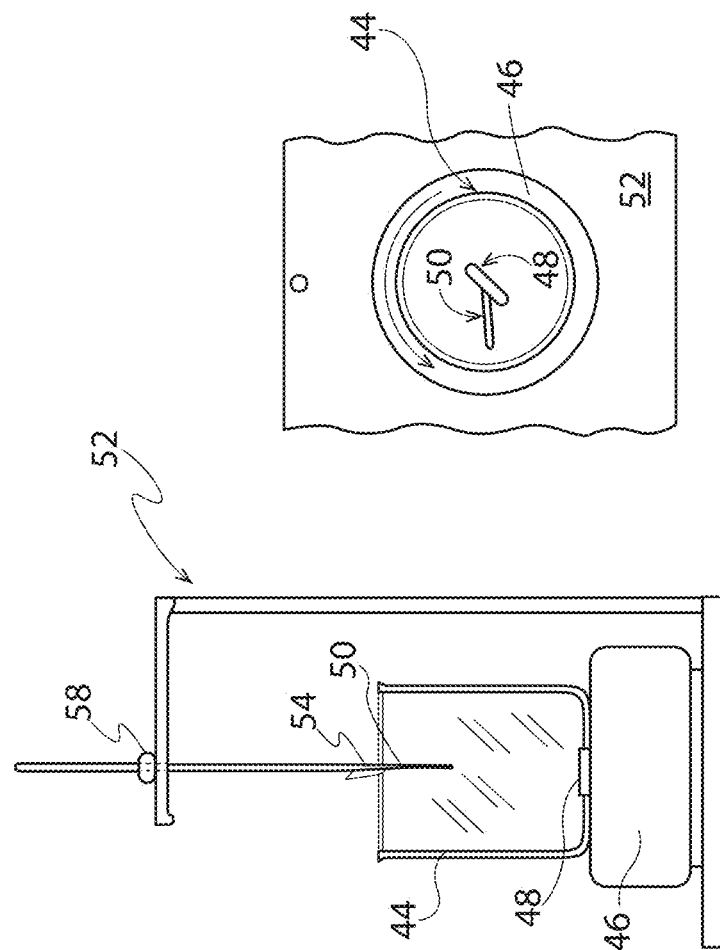
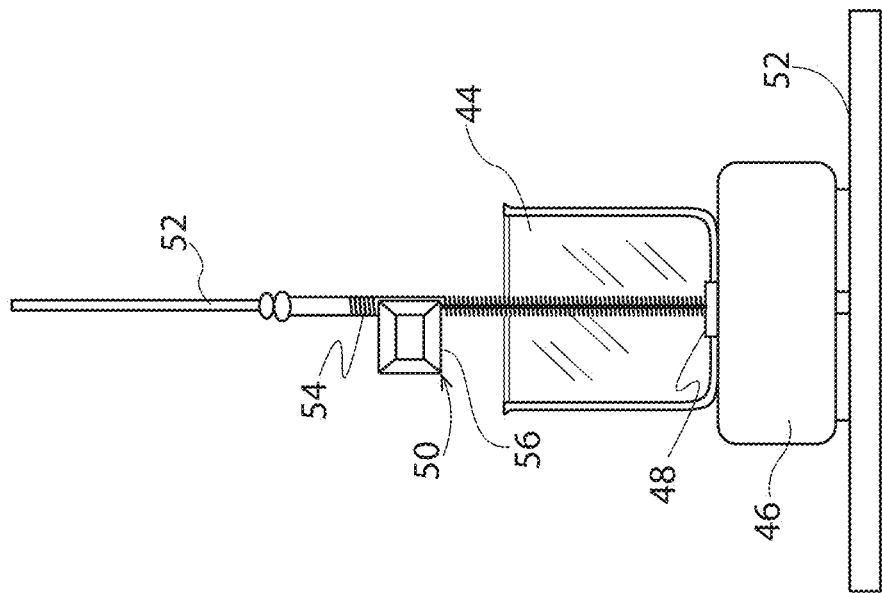
Fig. 14
Fig. 13
Fig. 12

COMPOSITIONS IN THE FORM OF DISSOLVABLE SOLID STRUCTURES

FIELD OF THE INVENTION

The present invention relates to compositions in the form of dissolvable solid structures.

The dissolvable solid structures comprise fibers formed from a composition comprising a surfactant and a water soluble polymeric structurant wherein the dissolvable solid structure has a bulk density of less than about 0.380 g/cm$^3$, a surfactant dose of from about 0.5 g to about 2.0 grams, and a surfactant density of from about 0.1 g/cm$^3$ to about 0.3 g/cm$^3$.

BACKGROUND OF THE INVENTION

Many personal care and other consumer products in the market today are sold in liquid form. While widely used, liquid products often have tradeoffs in terms of packaging, storage, transportation, and convenience of use. Liquid consumer products typically are sold in bottles which add cost as well as packaging waste, much of which ends up in land-fills.

Dissolvable solid products have been disclosed, comprising a water-soluble polymeric structurant and a surfactant or other ingredients. Although existing dissolvable products provide good performance benefits to end users, the processes for making them can have less than optimal cost, rate of manufacture, and/or product variability parameters.

The inventors surprisingly found that it is possible to deliver 1) sufficient cleansing in a unit-dose article that 2) readily dissolves in water, and 3) fits in a typical consumer hand. These benefits are achieved when a dissolvable solid structures comprises fibers formed from a composition comprising a surfactant and a water soluble polymeric structurant, wherein the dissolvable solid structure has a bulk density of less than about 0.380 g/cm$^3$, a surfactant dose of from about 0.5 g to about 2.0 grams, and a surfactant density of from about 0.1 g/cm$^3$ to about 0.3 g/cm$^3$.

SUMMARY OF THE INVENTION

A dissolvable solid structure comprising fibers wherein the fibers are formed from a composition comprising: from about 10% to about 75% of a surfactant; from about 10% to about 70% water soluble polymeric structurant; wherein the dissolvable solid structure comprises a detersive surfactant from about 0.5 g to about 4.0 g, has a detersive surfactant density from about 0.1 to about 0.3 g/cm$^3$; the bulk density of the dissolvable solid structure is from about 0.100 to about 0.380 g/cm$^3$, the dissolvable solid structure weight is from about 1.0 g to about 4.0 g, and wherein the footprint of the dissolvable solid structure is from about 1 cm$^2$ to about 50 cm$^2$.

BRIEF DESCRIPTION OF THE DRAWINGS

FIG. 9 is a schematic representation of an aperturing process according to the present invention;

FIG. 12 is a front view of an example of a setup of equipment used in measuring dissolution according to the present invention;

FIG. 13 is a side view of FIG. 12;

FIG. 14 is a partial top view of FIG. 12.

DETAILED DESCRIPTION OF THE INVENTION

A. Definitions

Figure 1:
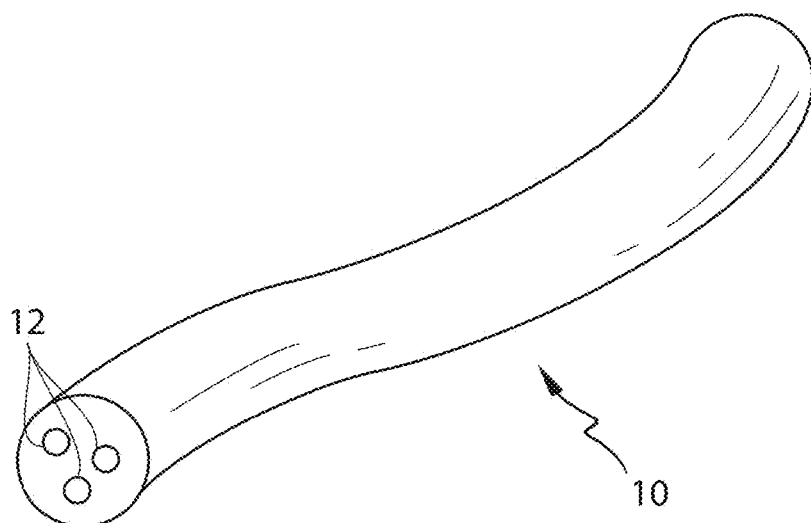
FIG. 1 is a schematic representation of an example of a fibrous element according to the present invention.
Figure 2:
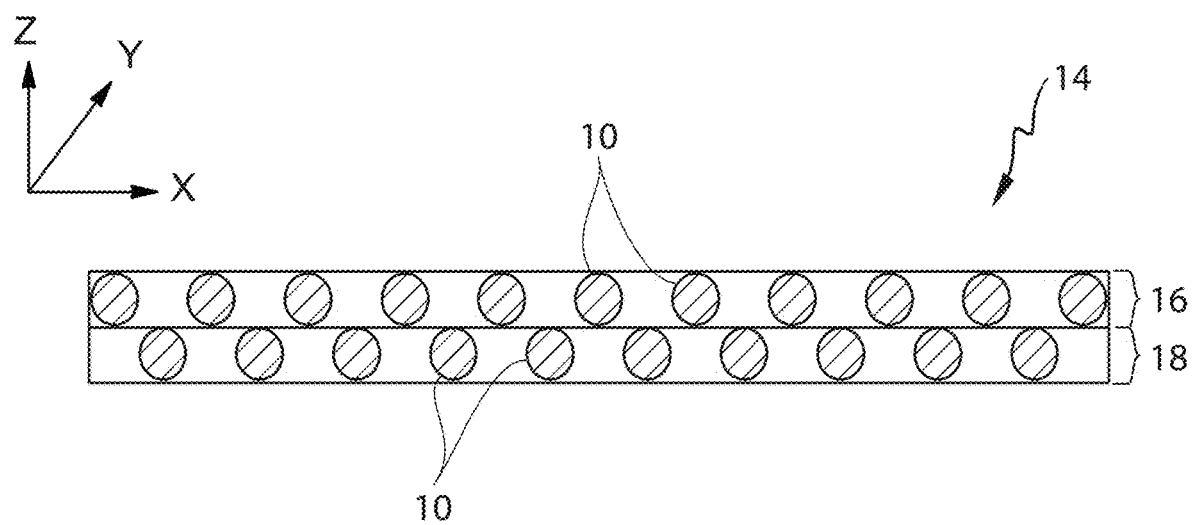
FIG. 2 is a schematic representation of an example of a fibrous structure according to the present invention.
Figure 3A:
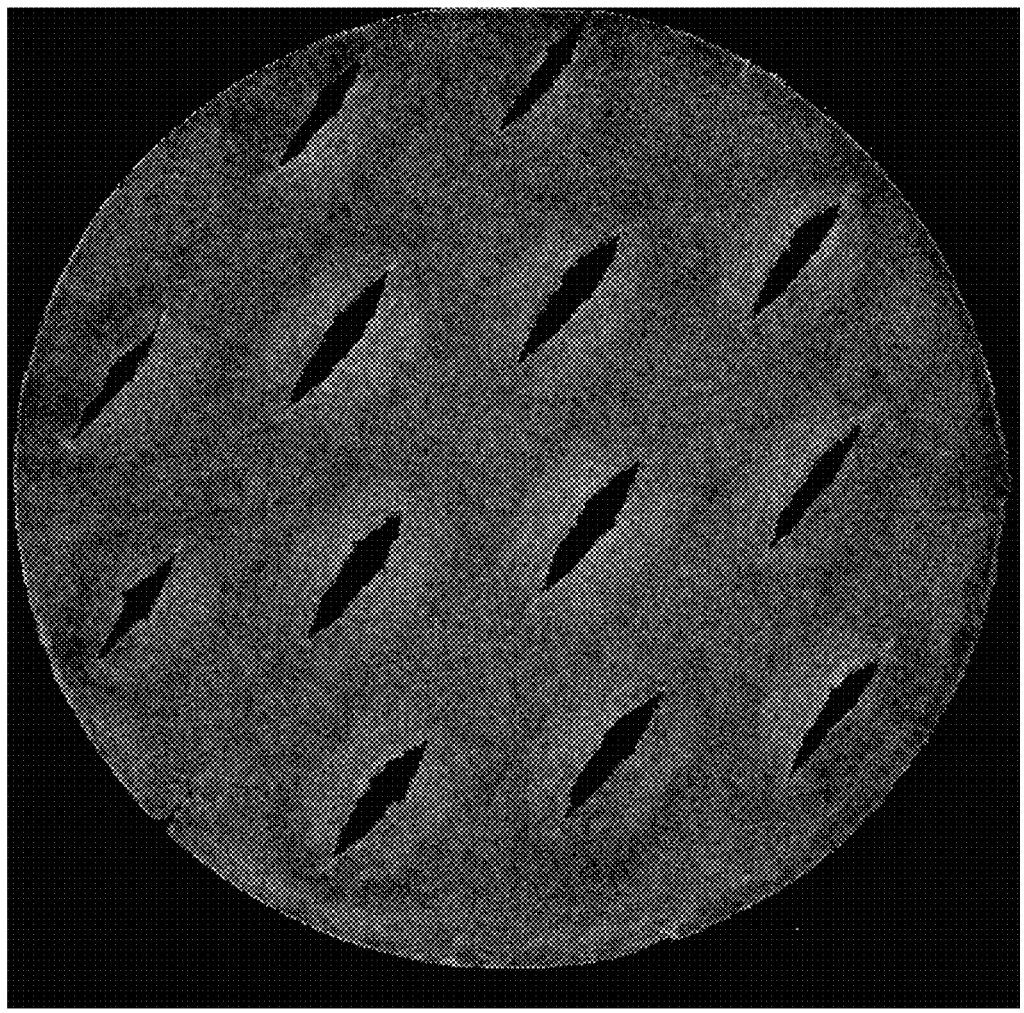
FIG. 3A is a microCT image of an example of a fibrous structure comprising apertures according to the present invention.
Figure 3B:
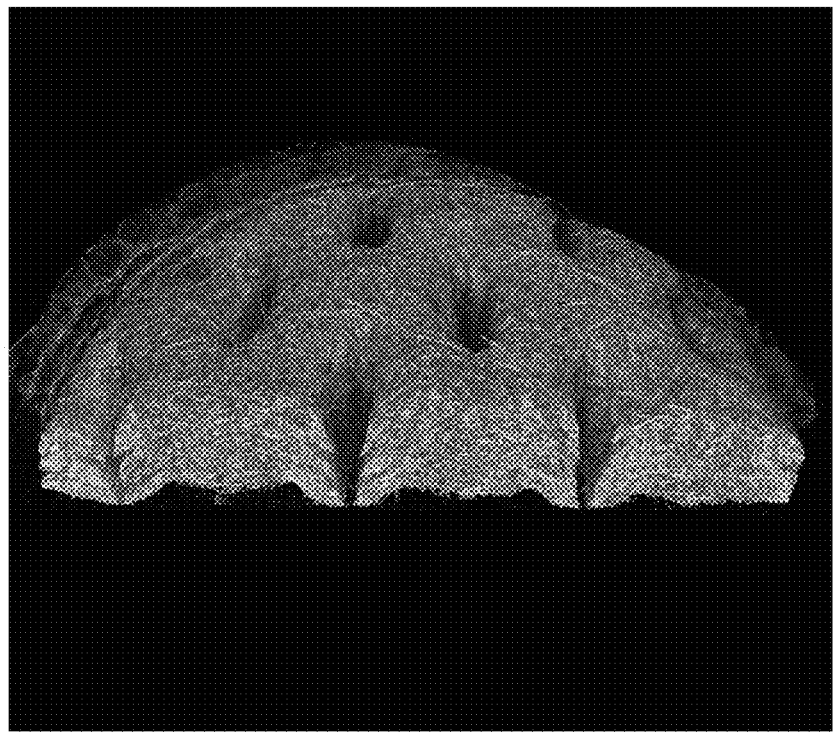
FIG. 3B is a partial, perspective view of the image of FIG. 3A.
Figure 3C:
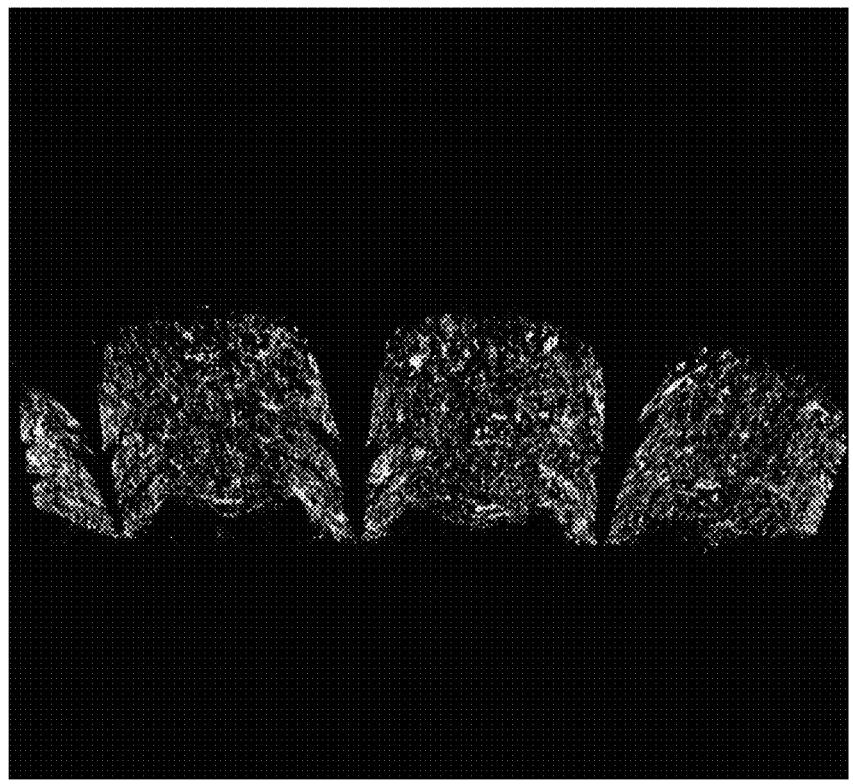
FIG. 3C is a cross-sectional view of the image of FIG. 3B.
Figure 4:
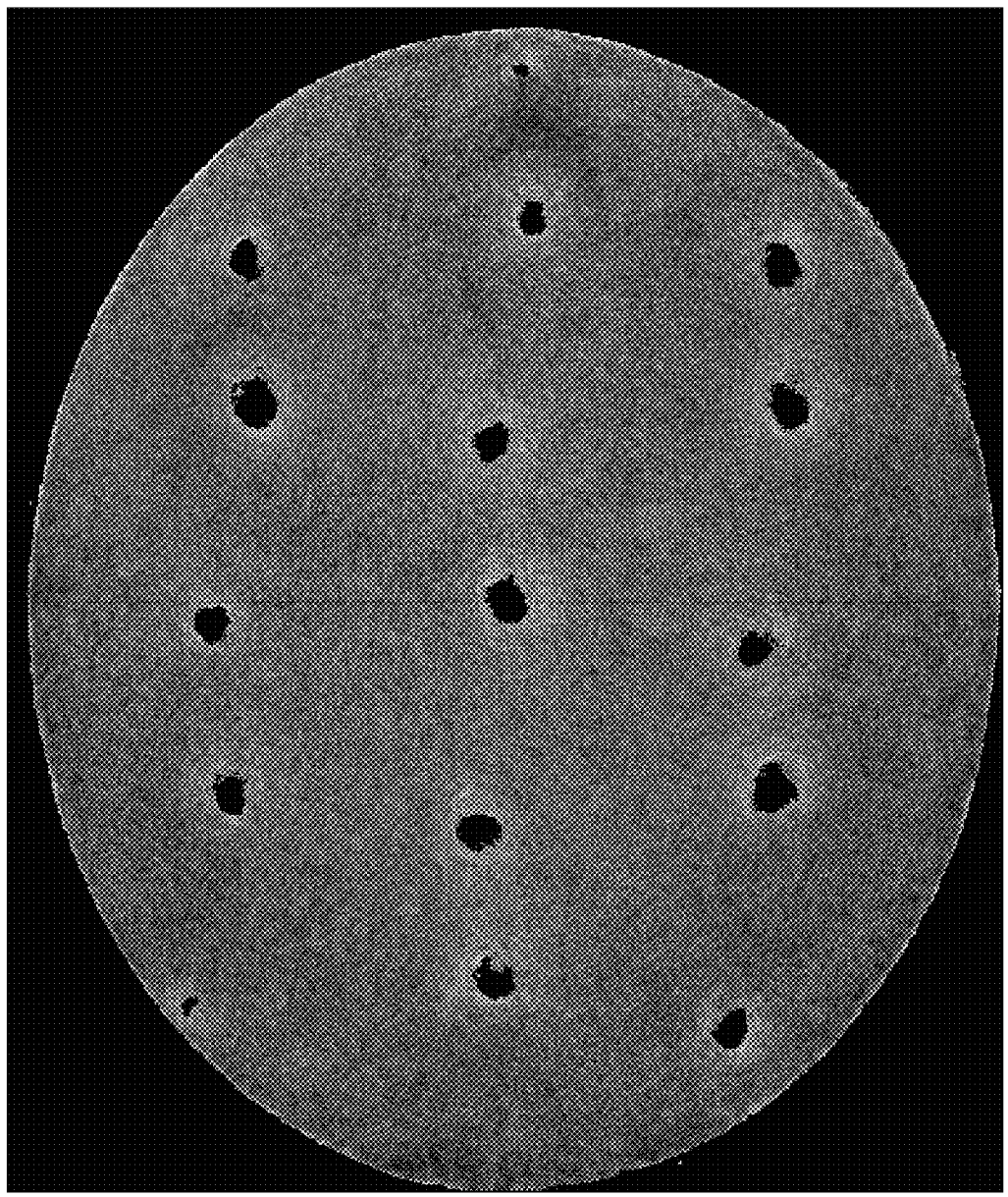
FIG. 4 is a microCT image of another example of a fibrous structure comprising apertures according to the present invention.
Figure 5:
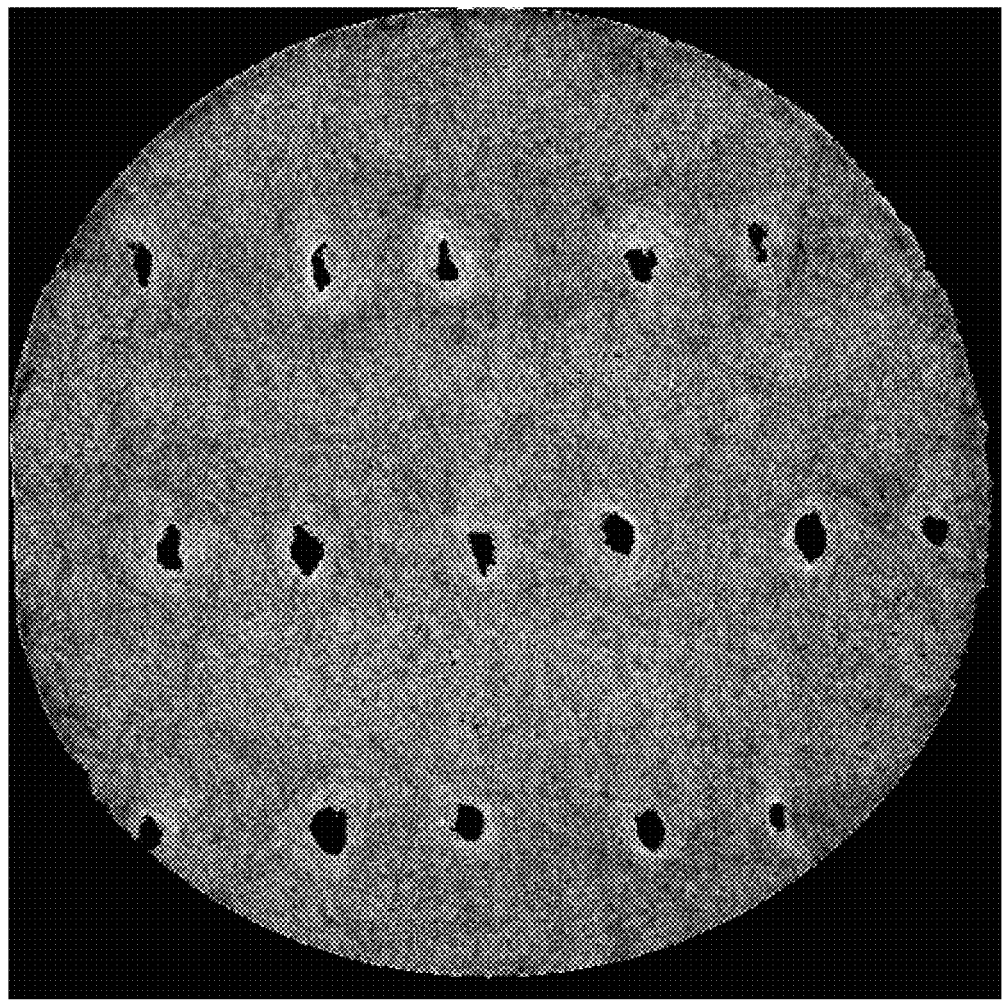
FIG. 5 is a microCT image of another example of a fibrous structure comprising apertures according to the present invention.
Figure 6:
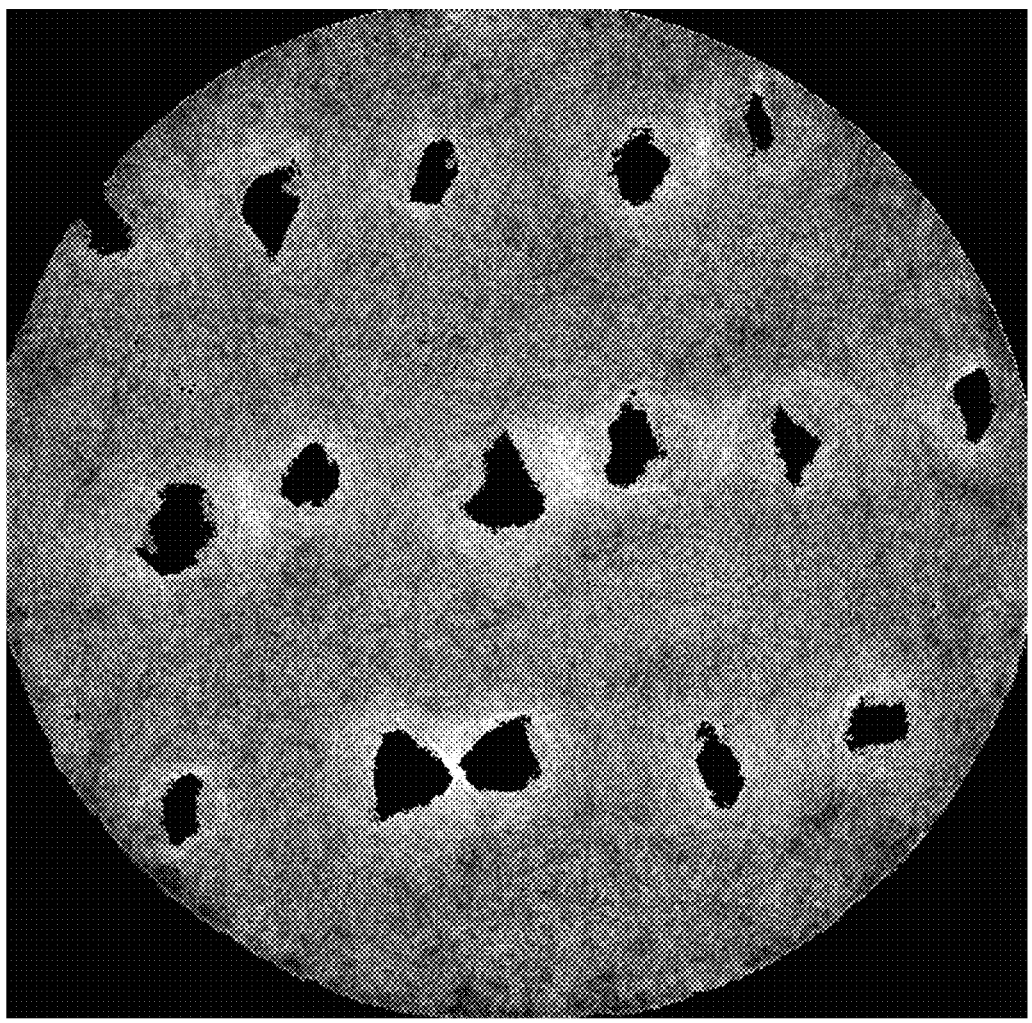
FIG. 6 is a microCT image of another example of a fibrous structure comprising apertures according to the present invention.
Figure 7:
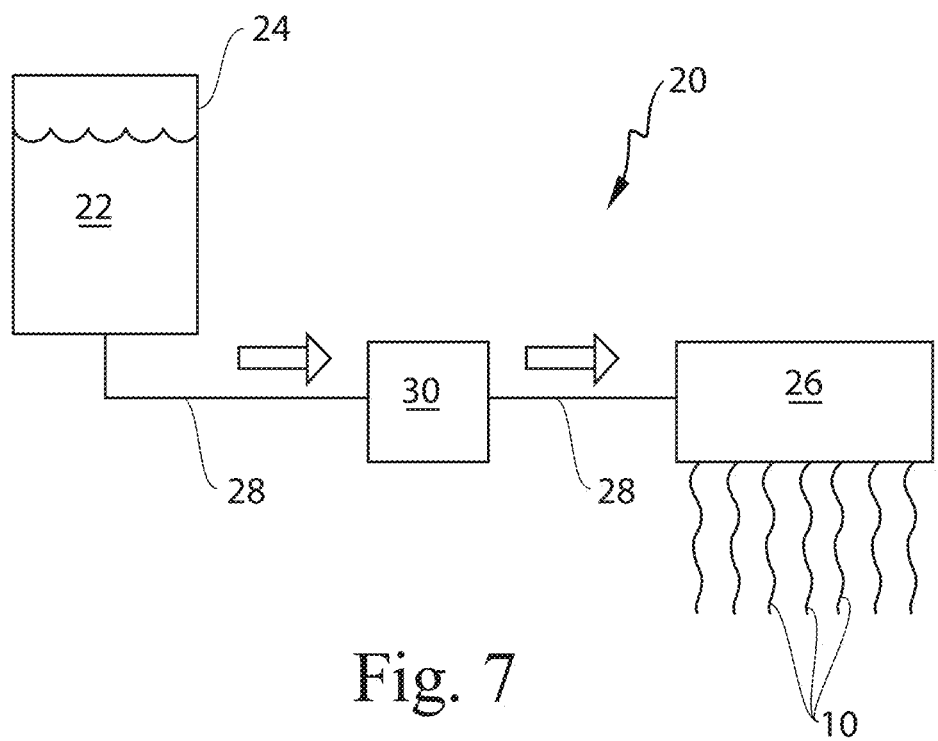
FIG. 7 is a schematic representation of an example of a process for making fibrous elements of the present invention.
Figure 8:
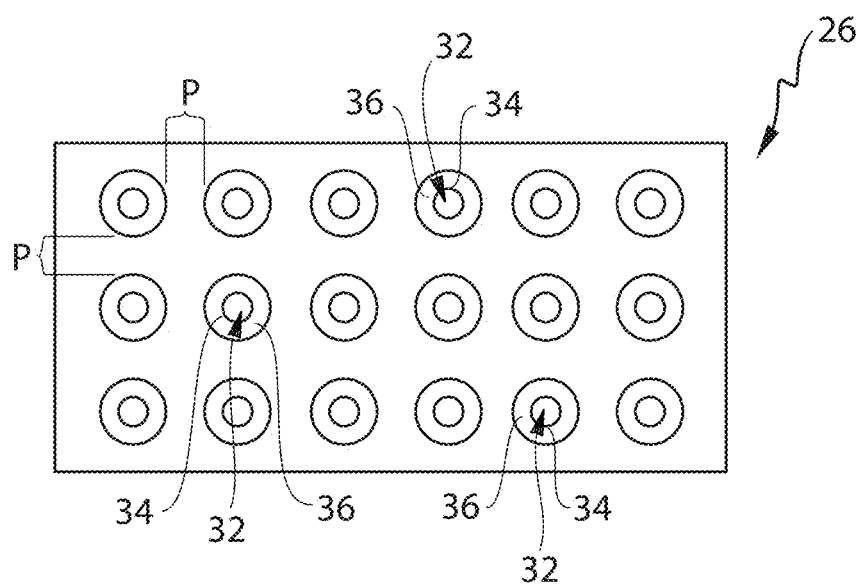
FIG. 8 is a schematic representation of an example of a die with a magnified view used in the process of FIG. 7.
Figure 10A:
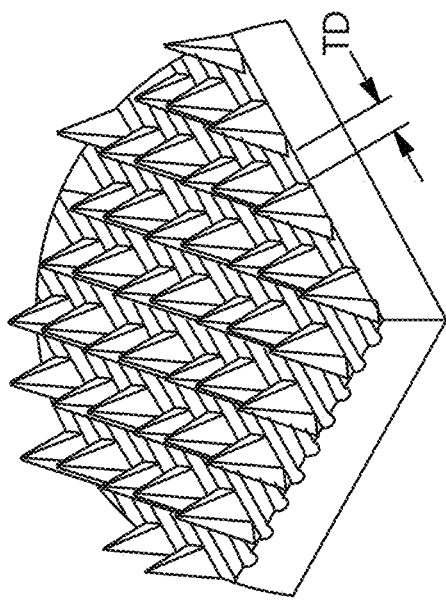
FIG. 10A is a perspective view of an example of a portion of a rotary knife aperturing apparatus.
Figure 10D:
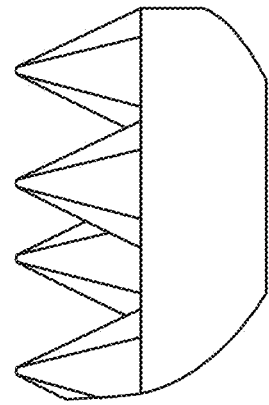
FIG. 10D is a side view of FIG. 10A.
Figure 10B:
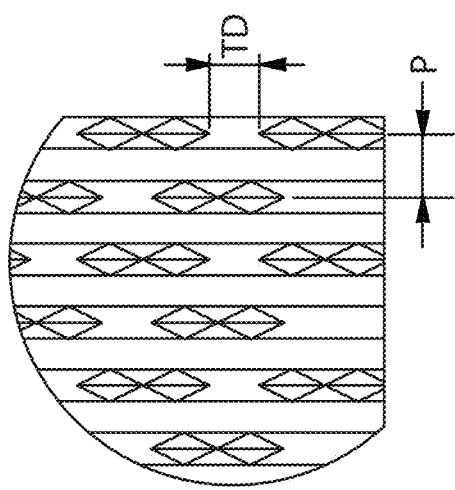
FIG. 10B is a top view of a portion of FIG. 10A.
Figure 10C:
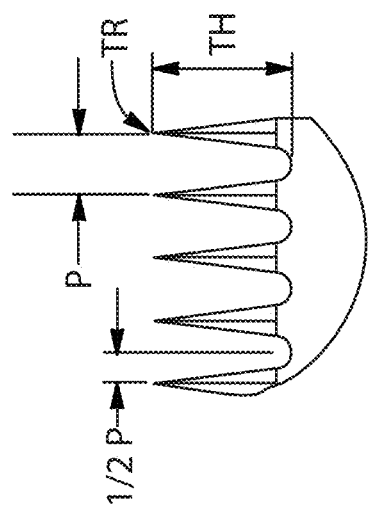
FIG. 10C is a front view of FIG. 10A.
Figure 11A:
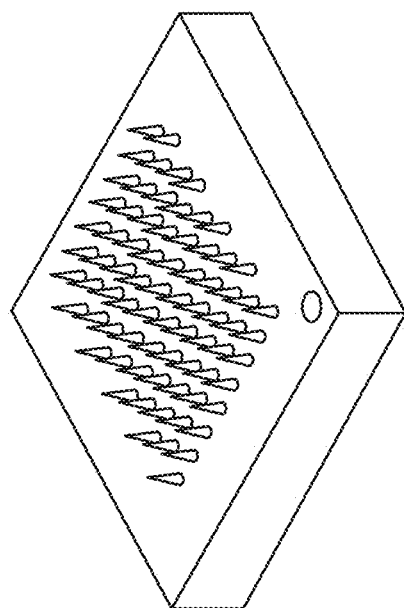
FIG. 11A is a perspective view of an example of a pinning aperturing apparatus.
Figure 11B:
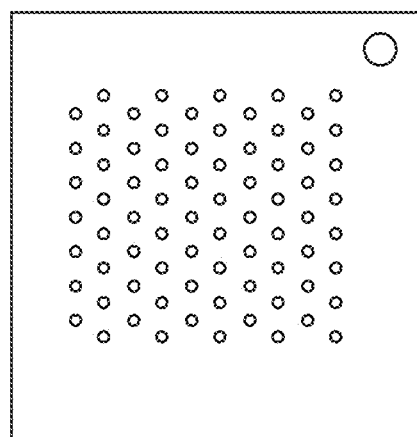
FIG. 11B is a top view of FIG. 11A.
Figure 11C:
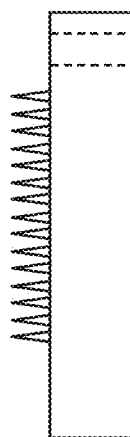
FIG. 11C is a side view of FIG. 11A.

As used herein, The Dissolvable Solid Structure may be referred to herein as "the Dissolvable Solid Structure", "the Structure", or "the Dissolvable Structure".

As used herein, "dissolvable" means that the Dissolvable Solid Structure meets the hand dissolution values discussed herein. The Dissolvable Solid Structure has a hand dissolution value of from about 1 to about 30 strokes, alternatively from about 2 to about 25 strokes, alternatively from about 3 to about 20 strokes, and alternatively from about 4 to about 15 strokes, as measured by the Hand Dissolution Method.

As used herein, "flexible" means a Dissolvable Solid Structure meets the distance to maximum force values discussed herein.

"Fibrous structure" as used herein means a structure that comprises one or more fibrous elements and optionally, one or more particles. In one example, a fibrous structure according to the present invention means an association of fibrous elements and optionally, particles that together form a structure, such as a unitary structure, capable of performing a function.

The fibrous structures of the present invention may be homogeneous or may be layered. If layered, the fibrous structures may comprise at least two and/or at least three and/or at least four and/or at least five layers, for example one or more fibrous element layers, one or more particle layers and/or one or more fibrous element/particle mixture layers. A layer may comprise a particle layer within the fibrous structure or between fibrous element layers within a fibrous structure. A layer comprising fibrous elements may sometimes be referred to as a ply. A ply may be a fibrous structure which may be homogeneous or layered as described herein.

In one example, a single-ply fibrous structure according to the present invention or a multi-ply fibrous structure comprising one or more fibrous structure plies according to the present invention may exhibit a basis weight of less than 1800 g/m² as measured according to the Basis Weight Test Method described herein. In one example, the single- or multi-ply fibrous structure according to the present invention may exhibit a basis weight of greater than 10 g/m² to about 1800 g/m² and/or greater than 10 g/m² to about 1750 g/m² and/or greater than 500 g/m² to about 1800 g/m² as measured according to the Basis Weight Test Method.

In one example, the fibrous structure of the present invention is a "unitary fibrous structure."

"Unitary fibrous structure" as used herein is an arrangement comprising a plurality of two or more and/or three or more fibrous elements that are inter-entangled or otherwise associated with one another to form a fibrous structure and/or fibrous structure plies. A unitary fibrous structure of the present invention may be one or more plies within a multi-ply fibrous structure. In one example, a unitary fibrous structure of the present invention may comprise three or more different fibrous elements. In another example, a unitary fibrous structure of the present invention may comprise two or more different fibrous elements.

"Article" as used herein refers to a consumer use unit, a consumer unit dose unit, a consumer use saleable unit, a single dose unit, or other use form comprising a unitary fibrous structure and/or comprising one or more fibrous structures of the present invention.

"Fibrous element" as used herein means an elongate particulate having a length greatly exceeding its average diameter, i.e. a length to average diameter ratio of at least about 10. A fibrous element may be a filament or a fiber. In one example, the fibrous element is a single fibrous element rather than a yarn comprising a plurality of fibrous elements.

The fibrous elements of the present invention may be spun from a filament-forming compositions also referred to as fibrous element-forming compositions via suitable spinning process operations, such as meltblowing, spunbonding, electro-spinning, and/or rotary spinning.

The fibrous elements of the present invention may be monocomponent (single, unitary solid piece rather than two different parts, like a core/sheath bicomponent) and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to polyvinyl alcohol and also thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

"Fiber" as used herein means an elongate particulate as described above that exhibits a length of less than 5.08 cm (2 in.) and/or less than 3.81 cm (1.5 in.) and/or less than 2.54 cm (1 in.).

Fibers are typically considered discontinuous in nature. Non-limiting examples of fibers include staple fibers produced by spinning a filament or filament tow of the present invention and then cutting the filament or filament tow into segments of less than 5.08 cm (2 in.) thus producing fibers.

In one example, one or more fibers may be formed from a filament of the present invention, such as when the filaments are cut to shorter lengths (such as less than 5.08 cm in length). Thus, in one example, the present invention also includes a fiber made from a filament of the present invention, such as a fiber comprising one or more filament-forming materials and one or more additives, such as active agents. Therefore, references to filament and/or filaments of the present invention herein also include fibers made from such filament and/or filaments unless otherwise noted. Fibers are typically considered discontinuous in nature relative to filaments, which are considered continuous in nature.

"Filament-forming composition" and/or "fibrous element-forming composition" as used herein means a composition that is suitable for making a fibrous element of the present invention such as by meltblowing and/or spunbonding. The filament-forming composition comprises one or more filament-forming materials that exhibit properties that make them suitable for spinning into a fibrous element. In one example, the filament-forming material comprises a polymer. In addition to one or more filament-forming materials, the filament-forming composition may comprise one or more additives, for example one or more active agents. In addition, the filament-forming composition may comprise one or more polar solvents, such as water, into which one or more, for example all, of the filament-forming materials and/or one or more, for example all, of the active agents are dissolved and/or dispersed prior to spinning a fibrous element, such as a filament from the filament-forming composition.

In one example as shown in FIG. 1, a fibrous element, for example a filament 10 of the present invention made from a fibrous element-forming composition of the present invention is such that one or more additives for example one or more active agents, may be present in the filament rather than on the filament, such as a coating composition comprising one or more active agents, which may be the same or different from the active agents in the fibrous elements and/or particles. The total level of fibrous element-forming materials and total level of active agents present in the fibrous element-forming composition may be any suitable amount so long as the fibrous elements of the present invention are produced therefrom.

In one example, one or more additives, such as active agents, may be present in the fibrous element and one or more additional additives, such as active agents, may be present on a surface of the fibrous element. In another example, a fibrous element of the present invention may comprise one or more additives, such as active agents, that are present in the fibrous element when originally made, but then bloom to a surface of the fibrous element prior to and/or when exposed to conditions of intended use of the fibrous element.

"Filament-forming material" and/or "fibrous element-forming material" as used herein means a material, such as a polymer or monomers capable of producing a polymer that exhibits properties suitable for making a fibrous element. In one example, the filament-forming material comprises one or more substituted polymers such as an anionic, cationic, zwitterionic, and/or nonionic polymer. In another example, the polymer may comprise a hydroxyl polymer, such as a polyvinyl alcohol ("PVOH"), a partially hydrolyzed polyvinyl acetate and/or a polysaccharide, such as starch and/or a starch derivative, such as an ethoxylated starch and/or acid-thinned starch, carboxymethylcellulose, hydroxypropyl cellulose, hydroxyethyl cellulose. In another example, the polymer may comprise polyethylenes and/or terephthalates. In yet another example, the filament-forming material is a polar solvent-soluble material.

The Dissolvable Solid Structure may be referred to herein as "the Dissolvable Solid Structure" or "the dissolvable solid structure", "the Dissolvable Structure" or "the Structure".

As used herein, "vinyl acetate-vinyl alcohol copolymer" (and "copolymer" when used in reference thereto) refers to a polymer of the following structure (I):

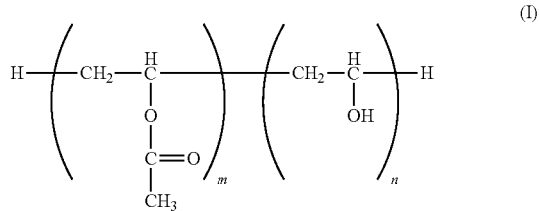

In structure (I), m and n are integers such that the polymeric structurant has the degree of polymerization and percent alcohol characteristics described herein. For purposes of clarity, this use of the term "copolymer" is intended to convey that the partially hydrolyzed polyvinyl acetate of the present invention comprises vinyl alcohol and vinyl acetate units. As discussed below, the polymeric structurant is routinely prepared by polymerizing vinyl acetate monomer followed by hydrolysis of some of the acetate groups to alcohol groups, as opposed to polymerization of vinyl acetate and vinyl alcohol monomer units (due in-part to the instability of vinyl alcohol).

As used herein a preformed effervescent agglomerated particle ("agglomerated particle") is an agglomerated particle that contains particles of both solid carbonate salt and solid acid along with a binder that is prepared prior to incorporation into the fibrous web.

As used herein, "molecular weight" or "M.Wt." refers to the weight average molecular weight unless otherwise stated. Molecular weight is measured using industry standard method, gel permeation chromatography ("GPC").

As used herein, the articles including "a" and "an" when used in a claim, are understood to mean one or more of what is claimed or described.

As used herein, the terms "include," "includes," and "including," are meant to be non-limiting.

The methods disclosed in the Test Methods Section of the present application should be used to determine the respective values of the parameters of Applicants' inventions, including those discussed in the Dissolvable Structures—Physical Characteristics section below.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

B. Dissolvable Solid Structure

Hair Care products in the form of a dissolvable solid structure present an attractive form to consumers. A typical use of these products includes a consumer holding the product in her hand, adding water to create a solution or dispersion and applying to the hair. In many cases, the products can take a long time to dissolve making it a less enjoyable experience for the consumer. Therefore, a need exists to have dissolvable solids that exhibit more rapid dissolution. The dissolvable solid structures are formed from fibers comprising surfactant and water soluble polymeric structurant. The dissolvable solid structures contain from about 0.5 g to about 4.0 g of surfactant, and has a detersive surfactant density of from about 0.1 to about 0.3 g/cm$^3$. The dissolvable solid structure has a bulk density of from about 0.100 to about 0.380 g/cm$^3$, a weight of from about 1.0 g to about 4.0 g and the footprint of the dissolvable solid structure is from about 1 cm$^2$ to about 50 cm$^2$, alternatively from about 10 cm$^2$ to about 50 cm$^2$.

The dissolvable solid structure can have a basis weight of from about 200/m$^2$ grams to about 1800 grams/m$^2$, alternatively from about 400 g/m$^2$ to about 1,800 g/m$^2$, alternatively from about 400 g/m$^2$ to about 1750 g/m$^2$, and alternatively from about 400 g/m$^2$ to about 1,650 g/m$^2$.

The dissolvable solid structure has a footprint of from about 1 cm$^2$ to about 50 cm$^2$, 10 cm$^2$ to about 50 cm$^2$, alternatively from about 15 cm$^2$ to about 25 cm$^2$, alternatively from about 17 cm$^2$ to about 23 cm$^2$. The bulk density of the dissolvable solid structure is from about 0.100 g/cm3 to about 0.380 g/cm$^3$, alternatively from about 0.100 g/cm$^3$ to about 0.375 g/cm$^3$, alternatively from about 0.300 g/cm$^3$ to about 0.375 g/cm$^3$.

The dissolvable solid structure has a hand dissolution value (as defined by the Hand Dissolution Method described herein) of less than about 25 strokes, alternatively less than about 15 strokes, alternatively from about 5 to about 25 strokes, alternatively from about 1 to about 25 strokes, alternatively from about 5 to about 15 strokes.

The dissolvable solid structure may comprise an effervescent agglomerated particle, which can improve dissolution and makes the in-use experience more interesting and enjoyable to the consumer. It has been surprisingly found that the inclusion of effervescent effect is significantly more pronounced when the effervescent components exist in an agglomerated form in the Dissolvable Solid Structure as compared to these components added separately and existing in the solid as separate particles from each other. It was also found that effervescent agglomerated particles and items that contain these agglomerated particles can pick up moisture from the environment and react prematurely, reducing the fast dissolution benefit. It was surprisingly found that the inclusion of humectants, such as zeolite, into the effervescent agglomerated particles prevents this premature reaction.

Dissolvable Structures—Compositional

The dissolvable solid structure can comprise fibers formed from about 3 wt % to about 75 wt % surfactant; and from about 10 wt % to about 70 wt % of the polymeric structurant.

The dissolvable solid structure can comprise from about 0.5 g to about 4.0 g of surfactant, alternatively from about 0.8 g to about 2.0 grams of surfactant, alternatively from about 0.9 g to about 1.5 g of surfactant, and alternatively from about 1.0 g to about 1.4 g of surfactant.

The dissolvable solid structure can comprise from about 1 wt % to about 40 wt % preformed effervescent agglomerated particles.

A. Water Soluble Polymeric Structurant

The Dissolvable Solid Structure comprises water-soluble polymers that function as a structurant. As used herein, the term "water-soluble polymer" is broad enough to include both water-soluble and water-dispersible polymers, and is defined as a polymer with a solubility in water, measured at 25° C., of at least about 0.1 gram/liter (g/L). In some embodiments, the polymers have solubility in water, measured at 25° C., of from about 0.1 gram/liter (g/L). to about 500 grams/liter (g/L). (This indicates production of a macroscopically isotropic or transparent, colored or colorless solution). The polymers for making these Dissolvable Solid Structures may be of synthetic or natural origin and may be modified by means of chemical reactions. They may or may not be film-forming. These polymers should be physiologically acceptable, i.e., they should be compatible with the skin, mucous membranes, the hair and the scalp.

The one or more water-soluble polymers may be present from about 5% to about 70% by weight of the Dissolvable Solid Structure, alternatively from about 15% to about 60% by weight, and alternatively from about 20% to about 50% by weight, and alternatively from about 15% to about 30% by weight.

The one or more water-soluble polymers can be selected such that their weight average molecular weight is from about 15,000 g/mol to about 500,000 g/mol, alternatively from about 50,000 g/mol to about 400,000 g/mol, alternatively from about 60,000 g/mol to about 300,000 g/mol, and alternatively from about 70,000 g/mol to about 200,000 g/mol. The weight average molecular weight is computed by summing the average molecular weights of each polymer raw material multiplied by their respective relative weight percentages by weight of the total weight of polymers present within the Dissolvable Solid Structure.

At least one of the one or more water-soluble polymers can be such that about 2% by weight solution of the water-soluble polymer gives a viscosity at 20° C. of from about 4 centipoise to about 80 centipoise; alternatively from about 5 centipoise to about 70 centipoise; and alternatively from about 6 centipoise to about 60 centipoise.

The water-soluble polymer(s) can include, but are not limited to, synthetic polymers as described in U.S. Ser. No. 61/120,786 including polymers derived from acrylic monomers such as the ethylenically unsaturated carboxylic monomers and ethylenically unsaturated monomers as described in U.S. Pat. No. 5,582,786 and EP-A-397410. The water-soluble polymer(s) which are suitable may also be selected from naturally sourced polymers including those of plant origin examples which are described in U.S. Ser. No. 61/120,786. Modified natural polymers are also useful as water-soluble polymer(s) and are included in U.S. Ser. No. 61/120,786. In one embodiment, water-soluble polymers include polyvinyl alcohols, polyacrylates, polymethacrylates, copolymers of acrylic acid and methyl acrylate, polyvinylpyrrolidones, polyalkylene oxides, starch and starch derivatives, pullulan, gelatin, hydroxypropylmethylcelluloses, methycelluloses, and carboxymethycelluloses. In another embodiment, water-soluble polymers include polyvinyl alcohols, and hydroxypropylmethylcelluloses. Suitable polyvinyl alcohols include those available from Celanese Corporation (Dallas, Tex.) under the CELVOL® trade name. Suitable hydroxypropylmethylcelluloses include those available from the Dow Chemical Company (Midland, Mich.) under the METHOCEL® trade name.

The above mentioned water-soluble polymer(s) may be blended with any single starch or combination of starches as a filler material in such an amount as to reduce the overall level of water-soluble polymers needed, so long as it helps provide the personal care Dissolvable Solid Structure with the requisite structure and physical/chemical characteristics as described herein.

In such instances, the combined weight percentage of the water-soluble polymer(s) and starch-based material generally ranges from about 10% to about 50%, alternatively from about 15% to about 40%, and alternatively from about 20% to about 30% by weight relative to the total weight of the Dissolvable Solid Structure. The weight ratio of the water-soluble polymer(s) to the starch-based material can generally range from about 1:10 to about 10:1, alternatively from about 1:8 to about 8:1, alternatively from about 1:7 to about 7:1, and alternatively from about 6:1 to about 1:6.

Typical sources for starch-based materials can include cereals, tubers, roots, legumes and fruits. Native sources can include corn, pea, potato, banana, barley, wheat, rice, sago, amaranth, tapioca, arrowroot, canna, sorghum, and waxy or high amylase varieties thereof. The starch-based materials may also include native starches that are modified using any modification known in the art, including those described in U.S. Ser. No. 61/120,786.

B. Surfactants

The Dissolvable Solid Structure comprises one or more detersive surfactants suitable for application to the hair or skin. Surfactants suitable for use in the Structure include anionic surfactants, nonionic surfactants, cationic surfactants, zwitterionic surfactants, amphoteric surfactants, polymeric surfactants or combinations thereof. Although representative surfactants are described herein, the skilled artisan will recognize that other surfactants can be readily substituted and similar benefits can be derived from use of the vinyl acetate-vinyl alcohol copolymers described herein. Each patent described throughout this application is incorporated herein by reference to the extent each provides guidance regarding surfactants suitable for inclusion in the Structure.

In one embodiment, the Structure is a lathering dissolvable solid personal care product (dried) and comprises from about 10 wt % to about 75 wt % surfactant, in one embodiment from about 25 wt % to about 70 wt % surfactant, in another embodiment from about 40 wt % to about 65 wt % surfactant.

Suitable anionic surfactants include alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one embodiment, the anionic surfactant is sodium lauryl sulfate or sodium laureth sulfate.

In one embodiment, the anionic surfactant is at least one branched sulfate having the formula $CH_3—(CH_2)_z—CH(R^1)—CH_2—O—(CH_2CH(R^2)O)_y—SO_3M$; where z is from about 3 to about 14; $R^1$ represents H or a hydrocarbon radical comprising 1 to 4 carbon atoms, $R^2$ is H or $CH_3$; $R^1$ and $R^2$ are not both H; y is 0 to about 7; the average value of y is about 1 when y is not=0; and M is a mono-valent or di-valent, positively-charged cation. Examples of mono-valent positively charged cations include ammonium, sodium, potassium, triethanolamine cation, and examples of di-valent positively charged cations include magnesium. For the foregoing branched sulfates, "average value" means that whereas the composition may comprise molecules having a value of y of other than 1, the average value of y all molecules in the composition is about 1.

Suitable amphoteric or zwitterionic surfactants include those which are known for use in shampoo or other cleansing products. Non limiting examples of suitable zwitterionic or amphoteric surfactants are described in U.S. Pat. Nos. 5,104,646 and 5,106,609, which are incorporated herein by reference in their entirety.

Suitable amphoteric surfactants include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants include cocoamphoacetate, cocoamphodiacetate, lauroamphoacetate, lauroamphodiacetate, and mixtures thereof.

Suitable zwitterionic surfactants include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

Suitable nonionic surfactants for use in the present invention include those described in McCutcheon's Detergents and Emulsifiers, North American edition (2010), Allured Publishing Corp., and McCutcheon's Functional Materials, North American edition (2010). Suitable nonionic surfactants for use in the Structure of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

In another embodiment, the nonionic surfactant is selected from sorbitan esters and alkoxylated derivatives of sorbitan esters including sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), sorbitan isostearate, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), all available from Uniqema, and combinations thereof.

Suitable copolymer surfactants include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

The surfactant can be a combination of surfactants wherein one or more surfactants from Group I, wherein Group I comprises anionic surfactants, and one or more surfactants from Group II, wherein Group II comprises a surfactant selected from the group consisting of amphoteric, zwitterionic and combinations thereof; wherein the ratio of Group I to Group II surfactants is from about 90:10 to about 30:70.

C. Agglomerated Particle

The Dissolvable Solid Structure has from about 1 wt % to about 80 wt % preformed effervescent agglomerated particles, alternatively from about 1 wt % to about 40 wt % preformed effervescent agglomerated particles alternatively from about 5 to about 25 wt % of preformed effervescent agglomerated particles, alternatively from about 10 to about 15 wt % of preformed effervescent agglomerated particles. Effervescent salts are widely used in the pharmaceutical and food industries. Suitable effervescent salts (carbonate salts) include, but are not limited to, sodium bicarbonate and sodium carbonate. The effervescence, or 'fizz', provides a signal to the consumer that the product is effective. The most common pairing of chemicals to produce the effervescent effect is Sodium Bicarbonate and Citric Acid, which are solid materials. The reaction equation is shown below:

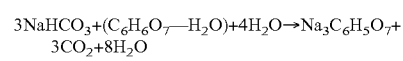

$$3NaHCO_3+(C_6H_6O_7—H_2O)+4H_2O \rightarrow Na_3C_6H_5O_7+3CO_2+8H_2O$$

The stoichiometry of the reaction indicates the weight ratio of 1:1.2 citric acid:sodium bicarbonate balances this equation.

A preformed effervescent agglomerated particle ("agglomerated particle") is an Agglomerated Particle that contains particles of both solid carbonate salt and solid acid along with a binder that is prepared prior to incorporation into the fibrous web. A carbonate salt is any metal salt of carbonic acid. A solid acid is any organic carboxylic acid that is solid in room temperature; e.g. it has a melting point of higher than 25° C. Preforming the effervescent agglomerated particle results in at consumer noticeable benefit from the Dissolvable Solid Structure. Suitable solid acids include, but are not limited to, tartaric acid, citric acid, fumaric acid, adipic acid, malic acid, oxalic acid, sulfamic acid and combinations thereof. Suitable carbonate salts include but are not limited to, sodium carbonate, calcium carbonate, magnesium carbonate, ammonium carbonate, potassium carbonate, sodium bicarbonate, potassium bicarbonate and calcium bicarbonate.

A binder is any material or substance that holds or draws other materials together to form a cohesive whole mechanically, chemically, or as an adhesive. The binder choice can have an effect on the foaming of the particle. Binders can include those that are nonionic to minimize the interaction with the reactants, however, polymeric and ionic binders can also be used. Suitable binders include, but are not limited to, Nonionic surfactants, nonionic polymers, Ethoxylated Alcohols, Sorbitan Derivates, Polyethylene Glycols, Corn Syrup, Paraffin, waxes, Fatty Alcohols, and mixtures thereof. Binders typically are included in the effervescent agglomerated particle at a level of from about 0.05 weight % of the effervescent agglomerated particle to about 10 weight % of the effervescent agglomerated particle, alternatively from about 1 weight % of the effervescent agglomerated particle to about 5 weight % of the effervescent agglomerated particle. Binders typically are included at from about 0.05 to about to about 5 weight % of the Dissolvable Solid Structure.

The agglomerated particles can be evenly distributed throughout the fiber matrix. The agglomerated particles may be distributed evenly on one layer or throughout multiple layers. For example one method is having it evenly distributed on all layers of the web. Alternatively, the agglomerated particle could be distributed through a middle layer, alternatively the agglomerated particle could be distributed only on an external layer outwardly facing layer.

The effervescent reaction is an acid/base neutralization reaction. During the reaction CO2 evolves, giving the characteristic effervescence desired in this product. The reaction will take place in the presence of moisture in the air, and auto-catalytically continue, at water activities above about 0.6 aW. Adding humectant to the effervescent agglomerated particle allows water from the air or from reacting materials to be absorbed, preventing or delaying the reaction. This improves process ability as well as shelf stability. The data below shows that increasing levels of humectant, in these examples Potassium Acetate, results in better stability of the effervescent agglomerated particles, as measured in mass loss due to CO2 release and flowability. Suitable humectants include Salts, sugars, acids, glycols, inorganics and combinations thereof. Suitable humectants can be selected from PEG400, PEG 600, Sorbitol, Potassium Carbonate, Sodium Chloride, Potassium Acetate, PEG 4000, zeolite, Corn syrup, Glycerol, Fructose, Sucrose, citric acid, tartaric acid, malic acid, lactic acid, Magnesium Chloride, and combinations thereof. Suitable humectant ranges are from about 0.1 to about 15 weight % of the effervescent agglomerated particle, alternatively from about 1 to about 7 weight % of the effervescent agglomerated particle. Suitable humectant ranges include from about 0.5 to about 10 weight % of the Dissolvable Solid Structure, alternatively from about 1 to about 7 weight % of the Dissolvable Solid Structure.

Flow aides can be included at low levels to help make the Agglomerated Particle flow better, non-limiting examples include Zeolite A, precipitated silica, precipitated silicates, fly ash, talc, starch, clays, metallic stearates, phosphates, amides, polysaccharides, sugars, and combinations thereof. Particularly suitable materials include Zeolite A, silica, sugars and mixtures thereof.

The effervescent agglomerated particle is based on the citric acid/sodium bicarbonate reaction shown above. There is a binder used to hold the particles together, a humectant added to provide stability with respect to moisture, and in some instances, a flow aide.

Method of Making Agglomerated Particles

Citric acid, sodium bicarbonate and humectant are mixed in a convective or tumbling solids mixer including paddle mixers or v-blenders for approximately 5 minutes. Binder is added and mixed for an additional 5 min, or longer for larger particles or shorter for smaller particles. The flow aid is added after Agglomerated Particle has reached target size. Mixing continues for approximately another minute. Agglomerated Particle is transferred into storage vessel until ready for use.

Particle size is controlled by the initial raw material particle size, binder selection, and the time of mixing after binder addition in agglomeration process. In one example, large Citric Acid, 400-500 μm, is chosen as a seed particle, the binder is nonionic binder to stick to smaller Sodium Bicarbonate particles, 50-100 μm, to the seed, and then coating the entire particle with Zeolite, less than about 10 μm, as a flow aid. Size is controlled primarily by citric acid size selection.

Suitable size is above 300 microns for the effervescent Agglomerated Particles for the typical process to have acceptable inclusion into the Dissolvable Solid Structure.

Suitable effervescent particles include those having a particle size of from about 100 microns to about 2000 microns. Suitable effervescent particles include those having a particle size of less than 2000 microns, alternatively less than 1000 microns, alternatively less than 800 micron. Large particles can have less consumer acceptance among some consumers because they are perceived as a gritty feel on their hands during dissolution. However, other consumers prefer larger particles preferably greater than 1000 microns, more preferably greater than 2000 microns so that as they feel them dissolve they know it is time to apply the product to hair. Suitable large particles can have a particle size of from about 1000 to about 5000 microns.

TABLE 5

| Ingredients | Agglomerated Particle Example | Agglomerated Particle Example | Agglomerated Particle Example |
|---|---|---|---|
| Citric acid | 41.7% | 41.7% | 41.7% |
| Sodium bicarbonate | 50.0% | 50.0% | 50.0% |
| Polysorbate- 80[1] | 1.0% | 1.0% | 1.0% |

TABLE 5-continued

| Ingredients | Agglomerated Particle Example | Agglomerated Particle Example | Agglomerated Particle Example |
|---|---|---|---|
| Sodium Aluminum Silicate[2] | 7.3% | 7.3% | 7.3% |
| Agglomerated Particle size[3] | 1000 micron | 600 micron | 300 micron |

[1]Tween-80 supplied by Croda
[2]Zeolite A supplied by Sasol
[3]Pass through standard screens of designated sizes.

Optional Ingredients

The Structure (dried) optionally comprises from about 1 wt % to about 25 wt % plasticizer, in one embodiment from about 3 wt % to about 20 wt % plasticizer, in one embodiment from about 5 wt % to about 15 wt % plasticizer.

When present in the Structures, non-limiting examples of suitable plasticizing agents include polyols, copolyols, polycarboxylic acids, polyesters and dimethicone copolyols.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., $C_2$-$C_8$ alcohols); mono di- and oligosaccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable plasticizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

EP 0283165 B1 discloses suitable plasticizers, including glycerol derivatives such as propoxylated glycerol.

The Structure may comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents (example zinc pyrithione and selenium sulfide etc.), perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials.

Suitable conditioning agents include high melting point fatty compounds, silicone conditioning agents and cationic conditioning polymers. Suitable materials are discussed in US 2008/0019935, US 2008/0242584 and US 2006/0217288.

Non-limiting examples of product type embodiments for use by the Structure include hand cleansing Structures, hair shampoo or other hair treatment Structures, body cleansing Structures, shaving preparation Structures, personal care Structures containing pharmaceutical or other skin care active, moisturizing Structures, sunscreen Structures, chronic skin benefit agent Structures (e.g., vitamin-containing Structures, alpha-hydroxy acid-containing Structures, etc.), deodorizing Structures, fragrance-containing Structures, and so forth.

The Structures are dissolvable, porous solid compositions wherein the porosity allows for liquid (e.g., water) flow during use such that the solid composition readily dissolves to provide a desired consumer experience. The porous nature of the Structure can be achieved in a variety of ways including, for example, forming an open celled foam or forming a fibrous structure.

For fibrous Structures, the Structure comprises a significant number of dissolvable fibers with an average diameter less than about 150 micron, alternatively less than about 100 micron, alternatively less than about 20 micron, alternatively less than about 10 micron, and alternatively less than about 1 micron with a relative standard deviation of less than 100%, alternatively less than 80%, alternatively less than 60%, alternatively less than 50%, such as in the range of 10% to 50%, for example. As set forth herein, the significant number means at least 10% of all the dissolvable fibers, alternatively at least 25% of all the dissolvable fibers, alternatively at least 50% of all the dissolvable fibers, alternatively at least 75% of all the dissolvable fibers. The significant number may be at least 99% of all the dissolvable fibers. Alternatively, from about 50% to about 100% of all the dissolvable fibers may have an average diameter less than about 20 micron. The dissolvable fibers produced by the method of the present disclosure have a significant number of dissolvable fibers with an average diameter less than about 1 micron, or sub-micron fibers. In an embodiment, Dissolvable Solid Structure may have from about 25% to about 100% of all the dissolvable fibers with an average diameter less than about 1 micron, alternatively from about 35% to about 100% of all the dissolvable fibers with an average diameter less than about 1 micron, alternatively from about 50% to about 100% of all the dissolvable fibers with an average diameter less than about 1 micron, and alternatively from about 75% to about 100% of all the dissolvable fibers with an average diameter less than about 1 micron.

The percent porosity of the dissolvable solid Structure is at least about 25%, alternatively at embodiment at least about 50%, alternatively at least about 60%, alternatively at least about 70% and alternatively at least about 80%. The porosity of the dissolvable solid Structure is not more than about 99%, alternatively not more than about 98%, alternatively not more than about 95%, and alternatively not more than about 90%. Porosity of a Structure is determined according to the procedure set forth in the definition of "porosity" above.

A range of effective sizes of pores can be accommodated. The pore size distribution through the Structure cross-section may be symmetric or asymmetric.

The Structure can be flexible and have a distance to maximum force value of from about 6 mm to about 30 mm. The distance to maximum force value from about 7 mm to about 25 mm, alternatively from about 8 mm to about 20 mm, and alternatively from about 9 mm to about 15 mm.

The Structure can be a flat, flexible Structure in the form of a pad, a strip, or tape and having a thickness of from about 0.5 mm to about 10 mm, alternatively from about 1 mm to about 9 mm, alternatively from about 2 mm to about 8 mm, and alternatively from about 3 mm to about 7 mm as measured by the below methodology. The Structure can be a sheet having a thickness from about 5 mm to about 6.5 mm. Alternatively two or more sheets are combined to form a Structure with a thickness of about 5 mm to about 10 mm.

Methods of Manufacture—Fibrous Structures

Method for Making Fibrous Elements

The fibrous elements of the present invention may be made by any suitable process. A non-limiting example of a suitable process for making the fibrous elements is described below.

The fibrous elements of the present invention may be made as follows. Fibrous elements may be formed by means of a small-scale apparatus. A pressurized tank, suitable for batch operation is filled with a suitable filament-forming composition according to the present invention. A pump such as a Zenith®, type PEP II, having a capacity of 5.0 cubic centimeters per revolution (cc/rev), manufactured by Parker Hannifin Corporation, Zenith Pumps division, of Sanford, N.C., USA may be used to facilitate transport of the filament-forming composition via pipes to a spinning die. The flow of the filament-forming composition from the pressurized tank to the spinning die may be controlled by adjusting the number of revolutions per minute (rpm) of the pump. Pipes are used to connect the pressurized tank, the pump, and the spinning die.

The spinning die can have several rows of circular extrusion nozzles (fibrous element-forming holes) spaced from one another at a pitch P of about 1.524 millimeters (about 0.060 inches). The nozzles have individual inner diameters of about 0.305 millimeters (about 0.012 inches) and individual outside diameters of about 0.813 millimeters (about 0.032 inches). Each individual nozzle is encircled by an annular and divergently flared orifice (concentric attenuation fluid hole to supply attenuation air to each individual melt capillary. The filament-forming composition extruded through the nozzles is surrounded and attenuated by generally cylindrical, humidified air streams supplied through the orifices.

A method for making a fibrous element 10 comprises the steps of:
a. providing a filament-forming composition comprising one or more filament-forming materials, and optionally one or more active agents; and
b. spinning the filament-forming composition, such as via a spinning die, into one or more fibrous elements, such as filaments 10, comprising the one or more filament-forming materials and optionally, the one or more active agents. The one or more active agents may be releasable from the fibrous element when exposed to conditions of intended use. The total level of the one or more filament-forming materials present in the fibrous element, for example filament 10, when active agents are present therein, may be less than 80% and/or less than 70% and/or less than 65% and/or 50% or less by weight on a dry fibrous element basis and/or dry fibrous structure basis and the total level of the one or more active agents, when present in the fibrous element may be greater than 20% and/or greater than 35% and/or 50% or greater 65% or greater and/or 80% or greater by weight on a dry fibrous element basis and/or dry fibrous structure basis.

The spinning die may comprise a plurality of fibrous element-forming holes that include a melt capillary encircled by a concentric attenuation fluid hole through which a fluid, such as air, passes to facilitate attenuation of the filament-forming composition into a fibrous element, for example a filament 10 as it exits the fibrous element-forming hole.

Attenuation air can be provided by heating compressed air from a source by an electrical-resistance heater, for example, a heater manufactured by Chromalox, Division of Emerson Electric, of Pittsburgh, Pa., USA. An appropriate quantity of steam was added to saturate or nearly saturate the heated air at the conditions in the electrically heated, thermostatically controlled delivery pipe. Condensate is removed in an electrically heated, thermostatically controlled, separator.

The embryonic fibrous elements are dried by a drying air stream having a temperature from about 149° C. (about 300° F.) to about 315° C. (about 600° F.) by an electrical resistance heater (not shown) supplied through drying nozzles and discharged at an angle of about 90° relative to the general orientation of the embryonic fibrous elements being extruded. The dried embryonic fibrous elements are collected on a collection device, such as, for example, a movable foraminous belt or patterned collection belt. The addition of a vacuum source directly under the formation zone may be used to aid collection of the fibers.

In one example, during the spinning step, any volatile solvent, such as water, present in the filament-forming composition is removed, such as by drying, as the fibrous element 10 is formed. In one example, greater than 30% and/or greater than 40% and/or greater than 60% of the weight of the filament-forming composition's volatile solvent, such as water, is removed during the spinning step, such as by drying the fibrous element being produced.

The filament-forming composition may comprise any suitable total level of filament-forming materials and any suitable level of active agents so long as the fibrous element produced from the filament-forming composition comprises a total level of filament-forming materials in the fibrous element of from about 5% to 50% or less by weight on a dry fibrous element basis and/or dry particle basis and/or dry fibrous structure basis and a total level of active agents in the fibrous element of from 50% to about 95% by weight on a dry fibrous element basis and/or dry particle basis and/or dry fibrous structure basis.

In one example, the filament-forming composition may comprise any suitable total level of filament-forming materials and any suitable level of active agents so long as the fibrous element produced from the filament-forming composition comprises a total level of filament-forming materials in the fibrous element and/or particle of from about 5% to 50% or less by weight on a dry fibrous element basis and/or dry particle basis and/or dry fibrous structure basis and a total level of active agents in the fibrous element and/or particle of from 50% to about 95% by weight on a dry fibrous element basis and/or dry particle basis and/or dry fibrous structure basis, wherein the weight ratio of filament-forming material to total level of active agents is 1 or less.

In one example, the filament-forming composition comprises from about 1% and/or from about 5% and/or from about 10% to about 50% and/or to about 40% and/or to about 30% and/or to about 20% by weight of the filament-forming composition of filament-forming materials; from about 1% and/or from about 5% and/or from about 10% to about 50% and/or to about 40% and/or to about 30% and/or to about 20% by weight of the filament-forming composition of active agents; and from about 20% and/or from about 25% and/or from about 30% and/or from about 40% and/or to about 80% and/or to about 70% and/or to about 60% and/or to about 50% by weight of the filament-forming composition of a volatile solvent, such as water. The filament-forming composition may comprise minor amounts of other active agents, such as less than 10% and/or less than 5% and/or less than 3% and/or less than 1% by weight of the filament-forming composition of plasticizers, pH adjusting agents, and other active agents.

The filament-forming composition is spun into one or more fibrous elements and/or particles by any suitable spinning process, such as meltblowing, spunbonding, electro-spinning, and/or rotary spinning In one example, the filament-forming composition is spun into a plurality of fibrous elements and/or particles by meltblowing. For example, the filament-forming composition may be pumped from a tank to a meltblown spinnerette. Upon exiting one or more of the filament-forming holes in the spinnerette, the filament-forming composition is attenuated with air to create one or more fibrous elements and/or particles. The fibrous elements and/or particles may then be dried to remove any remaining solvent used for spinning, such as the water.

The fibrous elements and/or particles of the present invention may be collected on a belt, such as a patterned belt to form a fibrous structure comprising the fibrous elements and/or particles.

Method for Making Fibrous Structures

A fibrous structure, for example a fibrous structure layer or ply of the present invention may be made by spinning a filament-forming composition from a spinning die, to form a plurality of fibrous elements, such as filaments 10. The fibrous elements may be spun via suitable spinning process operations, such as meltblowing, spunbonding, electro-spinning, and/or rotary spinning.

The dry embryonic fibrous elements, for example filaments may be collected on a molding member as described above. The construction of the molding member may provide areas that are air-permeable due to the inherent construction. The filaments that are used to construct the molding member will be non-permeable while the void areas between the filaments will be permeable. Additionally a pattern may be applied to the molding member to provide additional non-permeable areas which may be continuous, discontinuous, or semi-continuous in nature. A vacuum used at the point of lay down is used to help deflect fibers into the presented pattern.

In addition to the techniques described herein in forming regions within the fibrous structures having a different properties (e.g., average densities), other techniques can also be applied to provide suitable results. One such example includes embossing techniques to form such regions. Suitable embossing techniques are described in U.S. Patent Application Publication Nos. 2010/0297377, 2010/0295213, 2010/0295206, 2010/0028621, and 2006/0278355.

In one example, in a multi-ply article, one or more fibrous structure plies may be formed and/or deposited directly upon an existing ply of fibrous structure to form a multi-ply fibrous structure. The two or more existing fibrous structure plies may be combined, for example via thermal bonding, gluing, embossing, aperturing, rotary knife aperturing, die cutting, die punching, needlepunching, knurling, pneumatic forming, hydraulic forming, laser cutting, tufting, and/or other mechanical combining process, with one or more other existing fibrous structure plies to form the multi-ply article of the present invention.

Pre-formed dissolvable fibrous web (comprised of dissolvable fibers and, optionally, agglomerate particles), having approximately ⅓ the total desired basis weight of the finished article, can be arranged in a face to face relationship with post-add minor ingredients disposed between layers, and laminated with a solid state formation process. The resulting laminate is cut into the finished article shape via die cutting.

Lamination and Formation of Apertures via Solid State Formation

The 3-layer web stack with minors disposed between layers can be passed together through a solid state formation process (see Rotary Knife Aperturing Apparatus below), forming roughly conical apertures in the article and causing inter-layer fiber interactions which result in a mechanically lamination article. Lamination aids (e.g. web plasticizing agents, adhesive fluids, etc.) may be additionally used to aid in secure lamination of layers.

Rotary Knife Aperturing Apparatus

Suitable solid state description in disclosed in U.S. Pat. No. 8,679,391. Also, suitable dissolvable web aperturing description is disclosed in US 2016/0101026A1.

The nip comprises (2) intermeshed 100 pitch toothed rolls The teeth on the toothed rolls have a pyramidal shape tip with six sides that taper from the base section of the tooth to a sharp point at the tip. The base section of the tooth has vertical leading and trailing edges and is joined to the pyramidal shape tip and the surface of the toothed roller. The teeth are oriented so the long direction runs in the MD.

The teeth are arranged in a staggered pattern, with a CD pitch P of 0.100 inch (2.5 mm) and a uniform tip to tip spacing in the MD of 0.223 inch (5.7 mm). The overall tooth height TH (including pyramidal and vertical base sections) is 0.270 inch (6.9 mm), the side wall angle on the long side of the tooth is 6.8 degrees and the side wall angle of the leading and trailing edges of the teeth in the pyramidal tip section is 25 degrees.

The opposing toothed rolls are aligned such that the corresponding MD rows of teeth are in different planes and said planes are approximately equidistant from neighboring planes of the opposing roller; that is, such that the clearances on either side of the teeth are about equal. The degree of interference between the virtual cylinders described by the tips of the pins is described as the Depth of Engagement.

As web passes through the nip formed between the opposing rollers, the teeth from each roller engage with and penetrate the web to a depth determined largely by the depth of engagement between the rollers and the nominal thickness of the web. The opposing toothed rolls are aligned such that the corresponding MD rows of teeth are in different planes and said planes are approximately equidistant from neighboring planes of the opposing roller; that is, such that the clearances on either side of the teeth are about equal.

The Optional Preparing of the Surface Resident Coating Comprising the Active Agent The preparation of the surface resident coating comprising the active agent may include any suitable mechanical, chemical, or otherwise means to produce a composition comprising the active agent(s) including any optional materials as described herein, or a coating from a fluid.

Optionally, the surface resident coating may comprise a water releasable matrix complex comprising active agent(s). In one embodiment, the water releasable matrix complexes comprising active agent(s) are prepared by spray drying wherein the active agent(s) is dispersed or emulsified within an aqueous composition comprising the dissolved matrix material under high shear (with optional emulsifying agents) and spray dried into a fine powder. The optional emulsifying agents can include gum arabic, specially modified starches, or other tensides as taught in the spray drying art (See Flavor Encapsulation, edited by Sara J. Risch and Gary A. Reineccius, pages 9, 45-54 (1988), which is incorporated herein by reference). Other known methods of manufacturing the water releasable matrix complexes comprising active agent(s) may include but are not limited to, fluid bed agglomeration, extrusion, cooling/crystallization methods and the use of phase transfer catalysts to promote interfacial polymerization. Alternatively, the active agent(s) can be adsorbed or absorbed into or combined with a water releasable matrix material that has been previously produced via a variety of mechanical mixing means (spray drying, paddle mixers, grinding, milling etc.). In one embodiment, the water releasable matrix material in either pellet or granular or other solid-based form (and comprising any minor impurities as supplied by the supplier including residual solvents and plasticizers) may be ground or milled into a fine powder in the presence of the active agent(s) via a variety of mechanical means, for instance in a grinder or hammer mill.

Where the Dissolvable Solid Structure has a particulate coating, the particle size is known to have a direct effect on the potential reactive surface area of the active agents and thereby has a substantial effect on how fast the active agent delivers the intended beneficial effect upon dilution with water. In this sense, the active agents with smaller particle sizes tend to give a faster and shorter lived effect, whereas the active agents with larger particle sizes tend to give a slower and longer lived effect. In one embodiment the surface resident coatings may have a particle size from about 1 $\mu$m to about 200 $\mu$m, in another embodiment from about 2 $\mu$m to about 100 $\mu$m, and in yet another embodiment from about 3 $\mu$m to about 50 $\mu$m.

In some embodiments, it is helpful to include inert fillers within the grinding process, for instance aluminum starch octenylsuccinate under the trade name DRY-FLO® PC and available from Akzo Nobel, at a level sufficient to improve the flow properties of the powder and to mitigate inter-particle sticking or agglomeration during powder production or handling. Other optional excipients or cosmetic actives, as described herein, can be incorporated during or after the powder preparation process, e.g., grinding, milling, blending, spray drying, etc. The resulting powder may also be blended with other inert powders, either of inert materials or other powder-active complexes, and including water absorbing powders as described herein.

In one embodiment, the active agents may be surface coated with non-hygroscopic solvents, anhydrous oils, and/or waxes as defined herein. This may include the steps of: (i) coating the water sensitive powder with the non-hydroscopic solvents, anhydrous oils, and/or waxes; (ii) reduction of the particle size of the active agent particulates, prior to, during, or after a coating is applied, by known mechanical means to a predetermined size or selected distribution of sizes; and (iii) blending the resulting coated particulates with other optional ingredients in particulate form. Alternatively, the coating of the non-hydroscopic solvents, anhydrous oils and/or waxes may be simultaneously applied to the other optional ingredients, in addition to the active agents, of the surface resident coating composition and with subsequent particle size reduction as per the procedure described above.

Where the coating is applied to the Structure as a fluid (such as by as a spray, a gel, or a cream coating), the fluid can be prepared prior to application onto the Structure or the fluid ingredients can be separately applied onto the Structure such as by two or more spray feed steams spraying separate components of the fluid onto the Structure.

Post-add minor ingredients can be applied to the surface of one or more web layers in the nascent article, typically an interior surface. Individual minor ingredients may be applied together to a single selected surface or to separate surfaces. Minor ingredients may be applied to interior or exterior surfaces. In the present examples, minors were applied to the same interior surface, namely to one side of the middle of three layers.

Post-add ingredients in the present examples include fragrance and amodimethicone, both fluid at room temperature. Additional minor ingredients could include alternative conditioning agents, co-surfactants, encapsulated fragrance vehicles, rheology modifiers, etc. Minor ingredients could include fluids, particulates, pastes, or combinations.

In the present examples, fragrance is applied by atomizing through a spray nozzle (example Nordson EFD spray nozzle) and directing the resulting droplets of perfume to the target web surface, essentially uniformly over the surface.

In the present examples, amodimethicone is applied by expressing the fluid through an extrusion nozzle (example ITW-Dynatec UFD hot melt glue nozzle), comprising a series of orifices, approximately 500 microns in diameter and spaced at 2.5 mm, resulting in stripes of fluid extending the length of the target web surface.

Alternate fluid dispensing technologies, application patterns, and characteristic dimensions are contemplated.

Methods of Use

The compositions described herein may be used for cleaning and/or treating hair, hair follicles, skin, teeth, and the oral cavity. The method for treating these consumer structure may comprise the steps of: a) applying an effective amount of the Structure to the hand, b) wetting the Structure with water to dissolve the solid, c) applying the dissolved material to the target consumer substrate such as to clean or treat it, and d) rinsing the diluted treatment composition from the consumer substrate. These steps can be repeated as many times as desired to achieve the desired cleansing and or treatment benefit.

According to yet another embodiment, a method is provided for providing a benefit to hair, hair follicles, skin, teeth, and/or the oral cavity, comprising the step of applying a composition according to the first embodiment to these target consumer substrates in need of regulating.

Described herein is a method for regulating the condition of hair, hair follicles, skin, teeth, the oral cavity, comprising the step of applying one or more compositions described herein to these target consumer substrates in need of regulation.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.5 grams to about 10 grams, in one embodiment from about 1.0 grams to about 5 grams, and in another embodiment from about 1.5 grams to about 3 grams.

VI. Product Types and Articles of Commerce

Non-limiting examples of product embodiments that utilize the Structures include hand cleansing substrates, teeth cleaning or treating substrates, oral cavity substrates, hair shampoo or other hair treatment substrates, body cleansing substrates, shaving preparation substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and so forth.

Described herein is an article of commerce comprising one or more Structures described herein, and a communication directing a consumer to dissolve the Structure and apply the dissolved mixture to hair, hair follicles, skin, teeth, the oral cavity, to achieve a benefit to the target consumer substrate, a rapidly lathering foam, a rapidly rinsing foam, a clean rinsing foam, and combinations thereof. The communication may be printed material attached directly or indirectly to packaging that contains the Structure or on the Structure itself. Alternatively, the communication may be an electronic or a broadcast message that is associated with the article of manufacture. Alternatively, the communication may describe at least one possible use, capability, distinguishing feature and/or property of the article of manufacture.

Test Methods

Basis Weight Measurement

In general, basis weight of a material or article (including the dissolvable solid structure) is measured by first cutting the sample to a known area, using a die cutter or equivalent, then measuring & recording the weight of the sample on a top-loading balance with a minimum resolution of 0.01 g, then finally by calculating the basis weight as follows: Basis Weight (g/m2)=weight of basis weight pad (g)

$$\text{Basis Weight}\left(\frac{g}{m^2}\right) = \frac{\text{Weight of pad (g)} \times 10{,}000\ \frac{cm^2}{m^2}}{\text{area of pad (cm}^2)}$$

Preferred pad sample sizes for basis weight determination are >10 cm2 and should be cut with a precision die cutter having the desired geometry. If the article to be measured is smaller than 10 cm2, a smaller sampling area can be used for basis weight determination with the appropriate changes to calculation.

In the present examples, basis weight was calculated based on the full article having a known area of 17.28 cm2. Thus, the basis weight calculation becomes:

$$\text{Basis Weight}\left(\frac{g}{m^2}\right) = \frac{\text{Weight of pad (g)} \times 10{,}000\ \frac{cm^2}{m^2}}{17.28\ cm^2}$$

Thickness (Caliper) Measurement

The present examples were measured using the Check-Line J-40-V Digital Material Thickness Gauge from Electromatic Equipment Co. (Cedarhurst, N.Y.).

The sample (such as the dissolvable solid structure) is placed between a top and bottom plate of the instrument which has a top plate designed to apply a pressure of 0.5 kPa over a 25 cm2 area. The distance between the plates, to the nearest 0.01 mm, at the time of measurement is recorded as the thickness of the sample. The time of measurement is determined as the time at which the thickness in mm stabilizes or 5 seconds, whichever occurs first.

Equivalent methods are described in detail in compendial method ISO 9073-2, Determination of thickness for nonwovens, or equivalent.

Bulk Density (Density) Determination

Bulk Density is determined by calculation given a Thickness and Basis Weight of the sample (the solid dissolvable structure) (using methods as described above) according to the following:

$$\text{Bulk Density}\left(\frac{g}{cm^3}\right) = \frac{\text{Basis Weight of the pad}\left(\frac{g}{m^2}\right)}{\text{Thickness of the pad (mm)} \times 0.1\ \frac{cm}{mm} \times 10{,}000\ \frac{cm^2}{m^2}}$$

Surfactant Density Determination

Surfactant density is determined by calculation, given a Bulk Density of the material and a surfactant activity (fraction of the article that is surfactant).

$$\text{Surfactant Density}\left(\frac{g}{cm^3}\right) = \text{Bulk Density}\left(\frac{g}{cm^3}\right) \times \text{Surfactant Activity}\left(\frac{g}{g}\right)$$

Method of Measuring the footprint of a dissolvable solid structure (or article)

The footprint of the dissolvable structure/article can be measured by measuring the dimensions of its base so that the base area (that is, the footprint) can be calculated. For example, in the case in which the base of the article is a parallelogram having right angles, the length of the unequal sides of the base (A and B) are measured by a ruler and the area of the base (footprint) is calculated as the product A×B. In the case in which the base of the article is a square, the length of a side (C) is measured by a ruler and the area of the base (footprint) is calculated as the square C2. Other examples of shapes can include circle, oval, etc.

Distance to Maximum Force Method

Measured via a Rupture Method on a Texture Analyzer using a TA-57R cylindrical probe with Texture Exponent 32 Software. The Structure should have a thickness of between 4 to 7 mm and cut in a circle with a diameter of at least 7 mm for this method; or carefully cut or stacked to be within this overall thickness and diameter range. The porous solid sample is carefully mounted on top of the cylinder with four screws mounted on top with the top lid affixed in place on top of the sample. There is a hole in the center of the cylinder and its lid which allows the probe to pass through and stretch the sample. The sample is measured with a pre-test speed of 1 mm per second, a test speed of 2 mm per second and a post test speed of 3 mm per second over a total distance of 30 mm. The distance to maximum force is recorded.

Hand Dissolution Test Method

Materials Needed:
  Articles to be tested: 3-5 articles (finished product samples) (dissolvable solid structures) are tested so that an average of the number of strokes for each if the individual article samples is calculated and recorded as the Average Hand Dissolution value for the article. For this method, the entire consumer saleable or consumer use article is tested. If the entire consumer saleable or consumer use article has a footprint greater than 50 cm$^2$, then first cut the article to have a footprint of 50 cm$^2$.
  Nitrile Gloves
  10 cc syringe
  Plastic Weigh boat (~3 in×3 in)
  100 mL Glass beaker
  Water (City of Cincinnati Water or equivalent having the following properties: Total Hardness=155 mg/L as CaCO2; Calcium content=33.2 mg/L; Magnesium content=17.5 mg/L;
Phosphate content=0.0462 mg/L)
Water used is 7 gpg hardness and 40° C. +/−5° C.
Protocol:
  Add 300-500 ml of water to glass beaker.
  Heat water in beaker until water is at a temperature of 40° C.+/−5° C.
  Transfer 10 mL of the water from the beaker into the weigh boat via the syringe.
  Within 10 seconds of transferring the water to the weigh boat, place article sample in palm of gloved hand (hand in cupped position in non-dominant hand to hold article sample).
  Using dominant hand, add water quickly from the weigh boat to the article sample and allow to immediately wet for a period of 5-10 seconds.
  Rub with opposite dominant hand (also gloved) in 2 rapid circular strokes.
  Visually examine the article sample in hand after the 2 strokes. If article sample is completely dissolved, record number of strokes=2 Dissolution Strokes. If not completely dissolved, rub remaining article sample for 2 more circular strokes (4 total) and observe degree of dissolution. If article sample contains no solid pieces after the 2 additional strokes, record number of strokes=4 Dissolution Strokes. If after the 4 strokes total, the article sample still contains solid pieces of un-dissolved article sample, continue rubbing remaining article sample in additional 2 circular strokes and check if there are any remaining solid pieces of article sample after each additional 2 strokes until article sample is completely dissolved or until reaching a total of 30 strokes, whichever comes first. Record the total number of strokes. Record 30 Dissolution Strokes even if solid article sample pieces remain after the maximum of 30 strokes.
  Repeat this process for each of the additional 4 article samples.
  Calculate the arithmetic mean of the recorded values of Dissolution Strokes for the 5 individual article samples and record as the Average Hand Dissolution Value for the article. The Average Hand Dissolution Value is reported to the nearest single Dissolution Stroke unit.

Lather Profile: Lather Volume

The Structure provides a lather profile as described hereafter. The lather volume assessment is performed on 15 g/10 inch flat Oriental virgin hair switches that have been treated with 0.098 g of artificial liquid sebum [10-22% olive oil, 18-20% coconut oil, 18-20% oleic acid, 5-9% lanolin, 5-9% squalene, 3-6% palmitic acid, 3-6% paraffin oil, 3-6% dodecane, 1-4% stearic acid, 1-4% cholesterol, 1-4% coconut fatty acid, 18-20% choleth-24]. The hair switch is rinsed with 9-11 grain, 100° F. water at 1.5 gallons/min for 20 seconds with a shower nozzle. For testing the liquid control products, 0.75 cm$^3$ of liquid product are applied to the center of the switch, the lower portion of hair on the switch is then rubbed over the product on the hair 10 times in a circular motion, followed by 40 strokes back and forth (a total of 80 strokes). Lather speed is recorded as the number of strokes when the first lather is obviously generated during the 80 strokes. Lather from operator's gloves is transferred to a graduated cylinder with a 3.5 cm inside diameter and with total capacities of either 70 mL, 110 ml, or 140 ml depending on the total amount of lather generated (height modification of standard sized graduated cylinders via a glass shop). Lather from hair is gathered using one downward stroke on the switch with a tight grip and is also placed into the cylinder. Total lather volume is recorded in milliliters. Three runs per test sample are performed and the mean of the three values is calculated. When testing the Structure, 0.20+/−0.01 grams of product are weighed with the aid of scissors if needed and applied to the switch and then 2 cm$^3$ of additional water are added to the product via syringe. The lathering technique is then performed as described for liquid products after a 10 second waiting time.

As used herein, the terms "substantially non-lathering" and "non-lathering" are used to mean a lather volume of from 0 ml to 20 ml.

Fibrous Structures—Fiber Diameter

For fibrous Structures, the diameter of dissolvable fibers in a sample of a web is determined by using a Scanning Electron Microscope (SEM) or an Optical Microscope and image analysis software. A magnification of 200 to 10,000 times is chosen such that the fibers are suitably enlarged for measurement. When using the SEM, the samples are sputtered with gold or a palladium compound to avoid electric charging and vibrations of the fibers in the electron beam. A manual procedure for determining the fiber diameters is used from the image (on monitor screen) taken with the SEM or the optical microscope. Using a mouse and a cursor tool, the edge of a randomly selected fiber is sought and then measured across its width (i.e., perpendicular to fiber direction at that point) to the other edge of the fiber. A scaled and calibrated image analysis tool provides the scaling to get actual reading in microns (μm). Several fibers are thus randomly selected across the sample of the web using the SEM or the optical microscope. At least two specimens from the web (or web inside a product) are cut and tested in this manner. Altogether at least 100 such measurements are made and then all data are recorded for statistic analysis. The recorded data are used to calculate average (mean) of the fiber diameters, standard deviation of the fiber diameters, and median of the fiber diameters. Another useful statistic is the calculation of the amount of the population of fibers that is below a certain upper limit. To determine this statistic, the software is programmed to count how many results of the fiber diameters are below an upper limit and that count (divided by total number of data and multiplied by 100%) is reported in percent as percent below the upper limit, such as percent below 1 micron diameter or %-submicron, for example. We denote the measured diameter (in microns) of an individual circular fiber as $d_i$.

In case the fibers have non-circular cross-sections, the measurement of the fiber diameter is determined as and set equal to the hydraulic diameter which is four times the cross-sectional area of the fiber divided by the perimeter of the cross of the fiber (outer perimeter in case of hollow fibers). The number-average diameter, alternatively average diameter is calculated as, $d_{num}$ $$\frac{\sum_{i=1}^{n} d_i}{n}$$

Non-Limiting Examples

| Ingredient | Ex 1 | Ex 2 | Ex 3 | Ex 4 | Ex 5 | Ex 6 | Ex 7 | Comp. Ex A | Comp. Ex B |
|---|---|---|---|---|---|---|---|---|---|
| Distilled Water | 4.38 | 4.38 | 4.38 | 4.38 | 4.38 | 4.38 | 4.38 | 4.38 | 4.38 |
| Sodium Benzoate, NF | 0.27 | 0.27 | 0.27 | 0.27 | 0.27 | 0.27 | 0.27 | 0.27 | 0.27 |
| Guar hydroxypropyltrimonium Chloride[1] | 0.80 | 0.80 | 0.80 | 0.80 | 0.80 | 0.80 | 0.80 | 0.80 | 0.80 |
| Polyquatenium76[2] | 0.15 | 0.15 | 0.15 | 0.15 | 0.15 | 0.15 | 0.15 | 0.15 | 0.15 |
| Polyvinyl Alcohol[3] | 10.2 | 10.2 | 10.2 | 10.2 | 10.2 | 10.2 | 10.2 | 10.2 | 10.2 |
| Polyvinyl Alcohol[4] | 10.2 | 10.2 | 10.2 | 10.2 | 10.2 | 10.2 | 10.2 | 10.2 | 10.2 |
| Lauryl Hydroxysultaine[5] | 10.3 | 10.3 | 10.3 | 10.3 | 10.3 | 10.3 | 10.3 | 10.3 | 10.3 |
| Sodium Chloride | 1.8 | 1.8 | 1.8 | 1.8 | 1.8 | 1.8 | 1.8 | 1.8 | 1.8 |
| Sodium Laureth 1 Sulfate | 18.8 | 18.8 | 18.8 | 18.8 | 18.8 | 18.8 | 18.8 | 18.8 | 18.8 |
| Sodium Laureth 3 Sulfate | 2.6 | 2.6 | 2.6 | 2.6 | 2.6 | 2.6 | 2.6 | 2.6 | 2.6 |
| Sodium Undecyl Sulfate | 11.6 | 11.6 | 11.6 | 11.6 | 11.6 | 11.6 | 11.6 | 11.6 | 11.6 |
| Amodimethicone[6] | 4.5 | 4.5 | 4.5 | 4.5 | 4.5 | 4.5 | 4.5 | 4.5 | 4.5 |
| Fragrance | 6.5 | 6.5 | 6.5 | 6.5 | 6.5 | 6.5 | 6.5 | 6.5 | 6.5 |
| Sodium bicarbonate | 9.1 | 9.1 | 9.1 | 9.1 | 9.1 | 9.1 | 9.1 | 9.1 | 9.1 |
| Citric Acid, Anhydous (Global) | 8.8 | 8.8 | 8.8 | 8.8 | 8.8 | 8.8 | 8.8 | 8.8 | 8.8 |
| thickness (mm) | 3.06 | 4.37 | 4.78 | 4.56 | 4.84 | 3.61 | 4.41 | 5.66 | 5.45 |
| Basis Weight (g/m$^2$) | 939 | 1422 | 1443 | 1443 | 1432 | 1109 | 1477 | 1958 | 1958 |
| Number of Layers | 2 | 3 | 3 | 3 | 4 | 3 | 3 | 4 | 4 |
| Surfactant dose (g) | 0.82 | 1.25 | 1.27 | 1.27 | 1.26 | 1.30 | 1.73 | 1.72 | 1.72 |
| Total article density (g/cm3) | 0.346 | 0.366 | 0.339 | 0.355 | 0.333 | 0.344 | 0.375 | 0.388 | 0.403 |
| surfactant density (g/cm3) | 0.156 | 0.165 | 0.154 | 0.161 | 0.151 | 0.156 | 0.170 | 0.176 | 0.183 |
| Pad Footprint | 17.28 | 17.28 | 17.28 | 17.28 | 17.28 | 23.05 | 23.05 | 17.28 | 17.28 |
| Total Pad weight (g) | 1.83 | 2.76 | 2.80 | 2.80 | 2.78 | 2.86 | 3.81 | 3.79 | 3.79 |
| hand dissolution | 8 | 20 | 8.7 | 13.3 | 9.3 | 10 | 21.3 | 29.3 | 30 |

[1]Jaguar C500 supplied by Solvay
[2]Mirapol AM-T supplied by Solvay
[3]PVA420H supplied by Kuraray
[4]PVA403 supplied by Kuraray
[5]Mackham LHS supplied by Solvay
[6]Y-14945 Amino Fluid supplied by Momentive
[7]Neodol 25-3 supplied by Shell
[8]Tween-80 supplied by Croda

Examples/Combinations

Paragraph A: A dissolvable solid structure comprising fibers wherein the fibers are formed from a composition comprising:
 a. from about 10% to about 75% of a surfactant;
 b. from about 10% to about 70% water soluble polymeric structurant;
wherein the dissolvable solid structure comprises a detersive surfactant from about 0.5 g to about 4.0 g, has a detersive surfactant density from about 0.1 to about 0.3 g/cm$^3$; the bulk density of the dissolvable solid structure is from about 0.100 to about 0.380 g/cm$^3$, the dissolvable solid structure weight is from about 1.0 g to about 4.0 g, and wherein the footprint of the dissolvable solid structure is from about 1 cm$^2$ to about 50 cm$^2$.

Paragraph B: The dissolvable solid structure of Paragraph A, having a dissolution of less than 25 strokes.

Paragraph C: The dissolvable solid structure of Paragraph A-B, wherein the dissolvable solid structure contains detersive surfactant from about 0.8 g to about 2 g.

Paragraph D: The dissolvable solid structure of Paragraph A-C, wherein the dissolvable solid structure contains detersive surfactant from about 0.9 g to about 1.5 g.

Paragraph E: The dissolvable solid structure of Paragraph A-D, wherein the dissolvable solid structure contains detersive surfactant from about 1.0 g to about 1.4 g.

Paragraph F: The dissolvable solid structure of Paragraph A-E, wherein the dissolvable solid structure has a detersive surfactant density from about 0.1 g/cm$^3$ to about 0.3 g/cm$^3$.

Paragraph G: The dissolvable solid structure of Paragraph A-F, wherein the dissolvable solid structure has a detersive surfactant density from about 0.12 g/cm$^3$ to about 0.25 g/cm$^3$.

Paragraph H: The dissolvable solid structure of Paragraph A-G, wherein the dissolvable solid structure has a detersive surfactant density from about 0.15 g/cm$^3$ to about 0.18 g/cm$^3$.

Paragraph I: The dissolvable solid structure of Paragraph A-H, wherein the footprint of the dissolvable solid structure is from about 10 cm$^2$ to about 50cm$^2$.

Paragraph J: The dissolvable solid structure of Paragraph A-I, wherein the footprint of the dissolvable solid structure is from about 17 cm$^2$ to about 23cm$^2$.

Paragraph K: The dissolvable solid structure of Paragraph A-J, wherein the wherein the bulk density of the dissolvable solid structure is from about 0.100 g/cm$^3$ to about 0.375 g/cm$^3$.

Paragraph L: The dissolvable solid structure of Paragraph A-K, wherein the wherein the bulk density of the dissolvable solid structure is from about 0.300 g/cm$^3$ to about 0.375 g/cm$^3$.

Paragraph M: The dissolvable solid structure of Paragraph A-L, wherein the dissolvable solid structure has a basis weight of from about 400 g/m2 to about 1800 g/m2.

Paragraph N: The dissolvable solid structure of Paragraph A-M, wherein the dissolvable solid structure has a basis weight of from about 400 g/m2 to about 1750 g/m2.

Paragraph O: The dissolvable solid structure of Paragraph A-N, wherein the dissolvable solid structure has a basis weight of from about 400 g/m2 to about 1650 g/m$^2$.

Paragraph P: The dissolvable solid structure of Paragraph A-O, comprising soluble polymeric structurant at from about 10% to about 30% by weight.

Paragraph Q: The dissolvable solid structure of Paragraph A-P, comprising soluble polymeric structurant at from about 15% to about 20% by weight.

Paragraph R: The dissolvable solid structure of Paragraph A-Q, wherein the soluble polymeric structurant is polyvinyl alcohol.

Paragraph S: The Dissolvable Solid Structure of Paragraph A-R, wherein the Dissolvable Solid Structure dissolves in less than about 15 strokes of the Hand Dissolution Method.

Paragraph T: The Dissolvable Solid Structure of Paragraph A-S, wherein the dissolvable solid structure comprises fibers having an average diameter less than about 20 micrometer.

Paragraph U: The Dissolvable Solid Structure of Paragraph A-T, wherein the Dissolvable Solid Structure is a personal care article selected from the group consisting of hand cleansing Structures, hair shampoo, hair conditioner, hair color treatment Structures, facial cleansing Structures, body cleansing Structures, shaving preparation Structures, dental care Structures, personal care Structures containing pharmaceutical or other skin care active, moisturizing Structures, sunscreen Structures, chronic skin benefit agent Structures, vitamin-containing Structures, alpha-hydroxy acid-containing Structures, deodorizing Structures, fragrance-containing Structures, and combinations thereof.

Paragraph V: The Dissolvable Solid Structure of Paragraph A-U, wherein the Dissolvable Solid Structure further comprises one or more active agents selected from the group consisting of, skin treatment actives, heat generating agents, color indicators, silicones, organic conditioning oils, perfumes, flavors, sensates, sweeteners, oral care actives, and combinations thereof.

Paragraph W: The Dissolvable Solid Structure of Paragraph A-V, wherein the one or more water soluble polymeric structurants selected from the group consisting of polyalkylene oxides, polyvinyl alcohols, polyacrylates, copolymers of acrylic acid and methacrylic acid, polyvinylpyrrolidones, starch and starch derivatives, pullulan, gelatin, hydroxypropylmethylcelluloses, methylcelluloses, carboxymethycelluloses, salts and combinations thereof.

Paragraph X: The Dissolvable Solid Structure of Paragraph A-W, wherein the one or more water soluble polymeric structurants has a weight-average molecular weight of from about 40,000 g/mol to about 500,000 g/mol.

Paragraph Y: The Dissolvable Solid Structure of Paragraph A-X, wherein the dissolvable solid structure comprises a mixture of fibers produced by one or more methods, wherein the fibers are mixed homogenously or in layers.

Paragraph Z: The dissolvable solid structure of Paragraph A-Y, comprising from about 1 wt % to about 80 wt % preformed effervescent agglomerated particles.

Paragraph AA: The dissolvable solid structure of Paragraph A-Z, comprising from about 5 wt % to about 25 wt % preformed effervescent agglomerated particles.

Paragraph BB: The dissolvable solid structure of Paragraph A-AA, wherein the detersive surfactant is an anionic surfactant selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Note that any actives and/or compositions disclosed herein can be used in and/or with the Structure, disclosed in the following U.S Patent Applications, including any publications claiming priority thereto: U.S. 61/229,981; U.S. 61/229,986; U.S. 61/229,990; U.S. 61/229,996; U.S. 61/230,000; and U.S. 61/230,004.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dissolvable fibrous structure comprising a plurality of meltblown dissolvable fibrous elements wherein the fibrous elements are formed from a fibrous element-forming composition and the fibrous elements comprise:
   a. from about 10% to about 75% of an active wherein the active comprises a surfactant;
   b. from about 14% to about 70% of a fibrous element-forming material consisting of one or more water soluble polymeric structurants;
   wherein the fibrous elements comprise from about 0.5 g to about 4.0 g surfactant;
   wherein the dissolvable fibrous structure comprises:
   a surfactant density from about 0.1 g/cm$^3$ to about 0.3 g/cm$^3$;
   a bulk density of the dissolvable fibrous structure is from about 0.100 g/cm$^3$ to about 0.380 g/cm$^3$;
   a weight from about 1.0 g to about 4.0 g;
   a footprint from about 1 cm$^2$ to about 50 cm$^2$;
   wherein the fibrous elements comprise filaments;
   wherein the plurality of fibrous elements are inter-entangled or otherwise associated with one another to form the fibrous structure.

2. The dissolvable fibrous structure of claim 1, wherein the fibrous elements comprise from about 0.8 g to about 2 g surfactant.

3. The dissolvable fibrous structure of claim 2, wherein the fibrous elements comprise from about 0.9 g to about 1.5 g surfactant.

4. The dissolvable fibrous structure of claim 3, wherein the fibrous elements comprise from about 1.0 g to about 1.4 g surfactant.

5. The dissolvable fibrous structure of claim 1, wherein the surfactant density is from about 0.12 g/cm$^3$ to about 0.25 g/cm$^3$.

6. The dissolvable fibrous structure of claim 5, wherein the surfactant density is from about 0.15 g/cm$^3$ to about 0.18 g/cm$^3$.

7. The dissolvable fibrous structure of claim 1, wherein the footprint of the dissolvable solid fibrous structure is from about 10 cm$^2$ to about 50 cm$^2$.

8. The dissolvable fibrous structure of claim 7, wherein the footprint of the dissolvable solid fibrous structure is from about 17 cm$^2$ to about 23 cm$^2$.

9. The dissolvable fibrous structure of claim 1, wherein the wherein the bulk density of the dissolvable solid fibrous structure is from about 0.100 g/cm$^3$ to about 0.375 g/cm$^3$.

10. The dissolvable fibrous structure of claim 1, wherein the wherein the bulk density of the dissolvable solid fibrous structure is from about 0.300 g/cm$^3$ to about 0.375 g/cm$^3$.

11. The dissolvable fibrous structure of claim 1, wherein the dissolvable solid fibrous structure further comprises a basis weight of from about 400 g/m$^2$ to about 1800 g/m$^2$.

12. The dissolvable fibrous structure of claim 1, wherein the dissolvable solid fibrous structure further comprises a basis weight of from about 400 g/m$^2$ to about 1750 g/m$^2$.

13. The dissolvable fibrous structure of claim 1, wherein the dissolvable solid fibrous structure further comprises a basis weight of from about 400 g/m$^2$ to about 1650 g/m$^2$.

14. The dissolvable fibrous structure of claim 1, comprising one or more soluble polymeric structurants at from about 10% to about 30% by weight.

15. The dissolvable fibrous structure of claim 1, wherein the dissolvable solid structure dissolves in less than about 25 strokes of the hand dissolution method.

16. The dissolvable fibrous structure of claim 15, wherein the dissolvable solid structure dissolves in less than about 15 strokes of the hand dissolution method.

17. The dissolvable fibrous structure of claim 1, wherein at least 50% of the fibrous elements comprise a diameter of less than 150 microns.

18. The dissolvable fibrous structure of claim 1, wherein the dissolvable solid fibrous structure is a hair conditioner and wherein the surfactant comprises a cationic surfactant.

19. The dissolvable fibrous structure of claim 1, wherein the one or more water soluble polymeric structurants is selected from the group consisting of polyalkylene oxides, polyvinyl alcohols, polyacrylates, copolymers of acrylic acid and methacrylic acid, polyvinylpyrrolidones, polyvinyl methyl ether, polyvinyl formamide, poly acrylamide, starch and starch derivatives, pullulan, gelatin, hydroxypropylmethylcelluloses, methylcelluloses, carboxymethycelluloses, salts and combinations thereof.

20. A dissolvable fibrous structure comprising a plurality of meltblown dissolvable fibrous elements wherein the fibrous elements are formed from a fibrous element-forming composition and the fibrous elements comprise:
   a. from about 25% to about 65% of an active wherein the active comprises a cationic surfactant;
   b. a fatty alcohol;
   c. from about 14% to about 30% of a fibrous element-forming material;
   wherein the fibrous elements comprise from about 0.5 g to about 4.0 g cationic surfactant;

wherein the dissolvable fibrous structure comprises:
a plurality of apertures extending from a top surface to the bottom surface;
a surfactant density from about 0.13 g/cm$^3$ to about 0.3 g/cm$^3$;
a bulk density of the dissolvable fibrous structure is from about 0.100 g/cm$^3$ to about 0.380 g/cm$^3$;
a weight from about 1.0 g to about 4.0 g;
a footprint from about 1 cm$^2$ to about 50 cm$^2$;
wherein the fibrous elements comprise filaments;
wherein the plurality of fibrous elements are inter-entangled or otherwise associated with one another to form the fibrous structure;
wherein the fibrous structure is a conditioner composition.

* * * * *